United States Patent
Gephart et al.

(10) Patent No.: US 7,041,206 B2
(45) Date of Patent: May 9, 2006

(54) MEDICAL DIAGNOSTIC SYSTEM

(75) Inventors: Chad Stephen Gephart, Boyertown, PA (US); H. William Loesch, Jenkintown, PA (US); Charles Francis McBrairty, Easton, PA (US); Edward James McBrairty, Souderton, PA (US); Michael J. Rello, Harleysville, PA (US); Thomas Kite Sharpless, Philadelphia, PA (US); Donald Wayne Shive, Fogelsville, PA (US)

(73) Assignee: Clinical Analysis Corporation, Quakertown, PA (US)

( * ) Notice: Subject to any disclaimer, the term of this patent is extended or adjusted under 35 U.S.C. 154(b) by 337 days.

(21) Appl. No.: 09/800,014

(22) Filed: Mar. 5, 2001

(65) Prior Publication Data

US 2001/0045355 A1 Nov. 29, 2001

Related U.S. Application Data

(60) Provisional application No. 60/219,357, filed on Jul. 19, 2000, provisional application No. 60/188,115, filed on Mar. 9, 2000.

(51) Int. Cl.
*G01N 27/327* (2006.01)

(52) U.S. Cl. .................. 204/406; 204/403.01; 204/407

(58) Field of Classification Search .......... 204/403.01, 204/403.02, 406, 407, 416, 418, 419, 417; 600/345, 347; 422/68.1, 82.01, 82.02, 82.03, 422/82.05; 702/104
See application file for complete search history.

(56) References Cited

U.S. PATENT DOCUMENTS

| 4,133,735 | A |   | 1/1979  | Afromowitz et al. |
|-----------|---|---|---------|-------------------|
| 4,225,410 | A |   | 9/1980  | Pace              |
| 4,454,007 | A |   | 6/1984  | Pace              |
| 4,797,188 | A | * | 1/1989  | Tomita ........................ 204/414 |
| 4,798,705 | A | * | 1/1989  | Jakubowicz et al. .......... 422/63 |
| 4,871,439 | A |   | 10/1989 | Enzer et al.      |
| 4,929,426 | A |   | 5/1990  | Bodai et al.      |
| 4,994,167 | A |   | 2/1991  | Shults et al.     |
| 5,074,977 | A |   | 12/1991 | Cheung et al.     |
| 5,096,669 | A |   | 3/1992  | Lauks et al.      |
| 5,108,889 | A | * | 4/1992  | Smith et al. .................... 435/4 |
| 5,269,891 | A |   | 12/1993 | Colin             |
| 5,284,624 | A |   | 2/1994  | Behnk             |
| 5,316,727 | A |   | 5/1994  | Suzuki et al.     |
| 5,325,853 | A |   | 7/1994  | Morris et al.     |

(Continued)

*Primary Examiner*—Kaj K. Olsen
(74) *Attorney, Agent, or Firm*—Akin Gump Strauss Hauer & Feld, LLP

(57) ABSTRACT

A system for conducting a plurality of different medical diagnostic tests comprises a hand-held portable self contained instrument for engaging a disposable test cell containing a fluid to be tested. The instrument performs a diagnostic test selected from the plurality of tests upon the fluid within the test cell, the test being selected by the instrument based upon identification information obtained from the test cell. A disposable, single use test cell is provided for receiving fluid to be diagnostically tested. The test cell includes identification information indicative of a particular test to be performed upon the fluid, the test cell being sized and shaped for engagement by the instrument.

33 Claims, 21 Drawing Sheets

U.S. PATENT DOCUMENTS

| | | |
|---|---|---|
| 5,377,128 A | 12/1994 | McBean |
| 5,384,031 A | 1/1995 | Anderson et al. |
| 5,405,510 A | 4/1995 | Betts et al. |
| 5,437,772 A | 8/1995 | DeCastro et al. |
| 5,519,635 A | 5/1996 | Miyake et al. |
| 5,591,403 A | 1/1997 | Gavin et al. |
| 5,632,957 A | 5/1997 | Heller et al. |
| 5,690,893 A | 11/1997 | Ozawa et al. |
| 5,695,623 A | 12/1997 | Michel et al. |
| 5,820,551 A | 10/1998 | Hill et al. |
| 5,849,208 A | 12/1998 | Hayes et al. |
| 5,873,990 A | 2/1999 | Wojciechowski et al. |
| RE36,268 E | 8/1999 | Szuminsky et al. |
| 5,985,130 A | 11/1999 | Ikeda et al. |
| 6,016,712 A | 1/2000 | Warden et al. |
| 6,060,327 A | 5/2000 | Keen |
| 6,066,243 A | 5/2000 | Anderson et al. |
| 6,066,448 A | 5/2000 | Wohlstadter et al. |
| 6,071,478 A | 6/2000 | Chow |
| 6,153,085 A * | 11/2000 | Patko et al. ................ 205/775 |

* cited by examiner

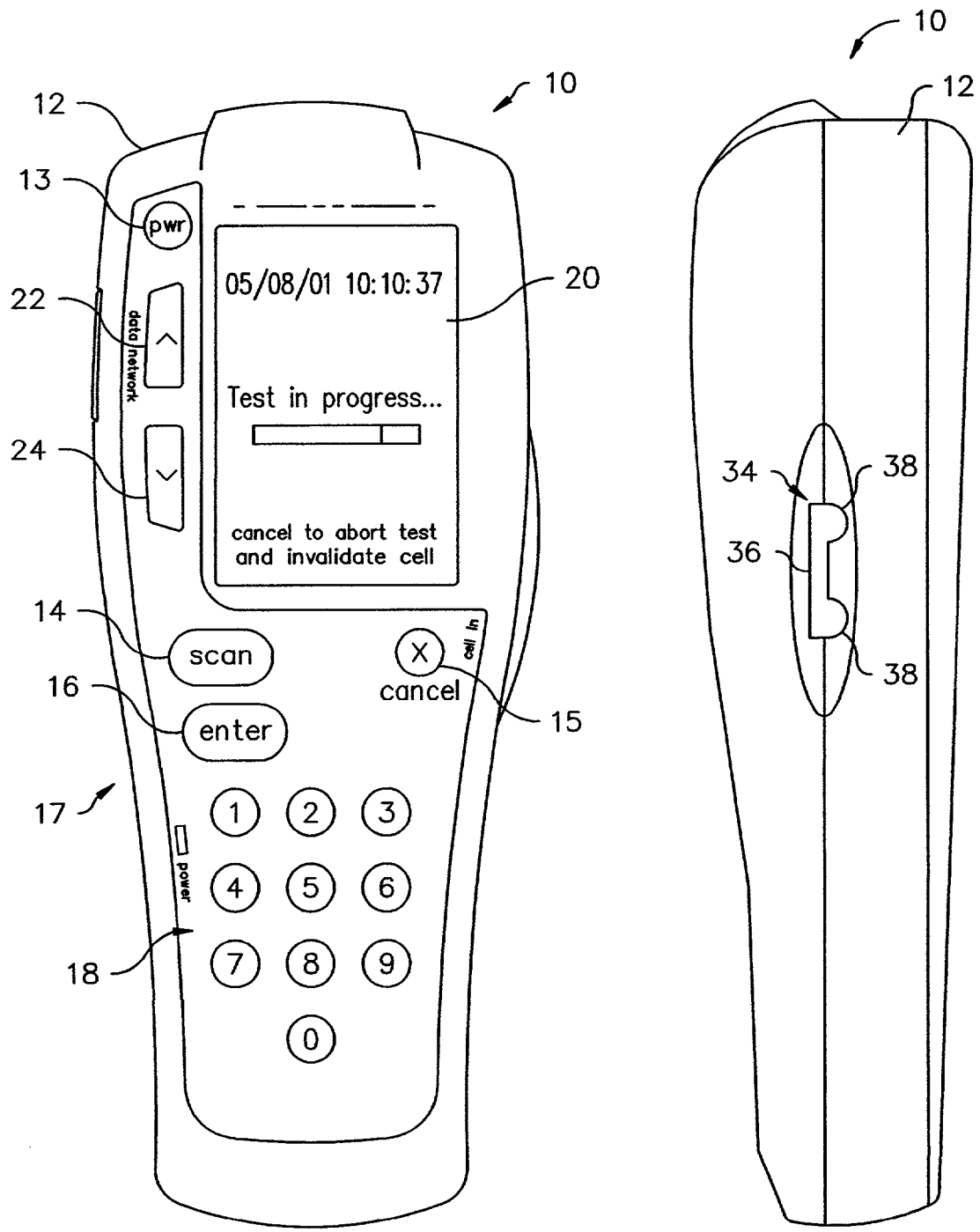
*Fig. 1*   *Fig. 2*

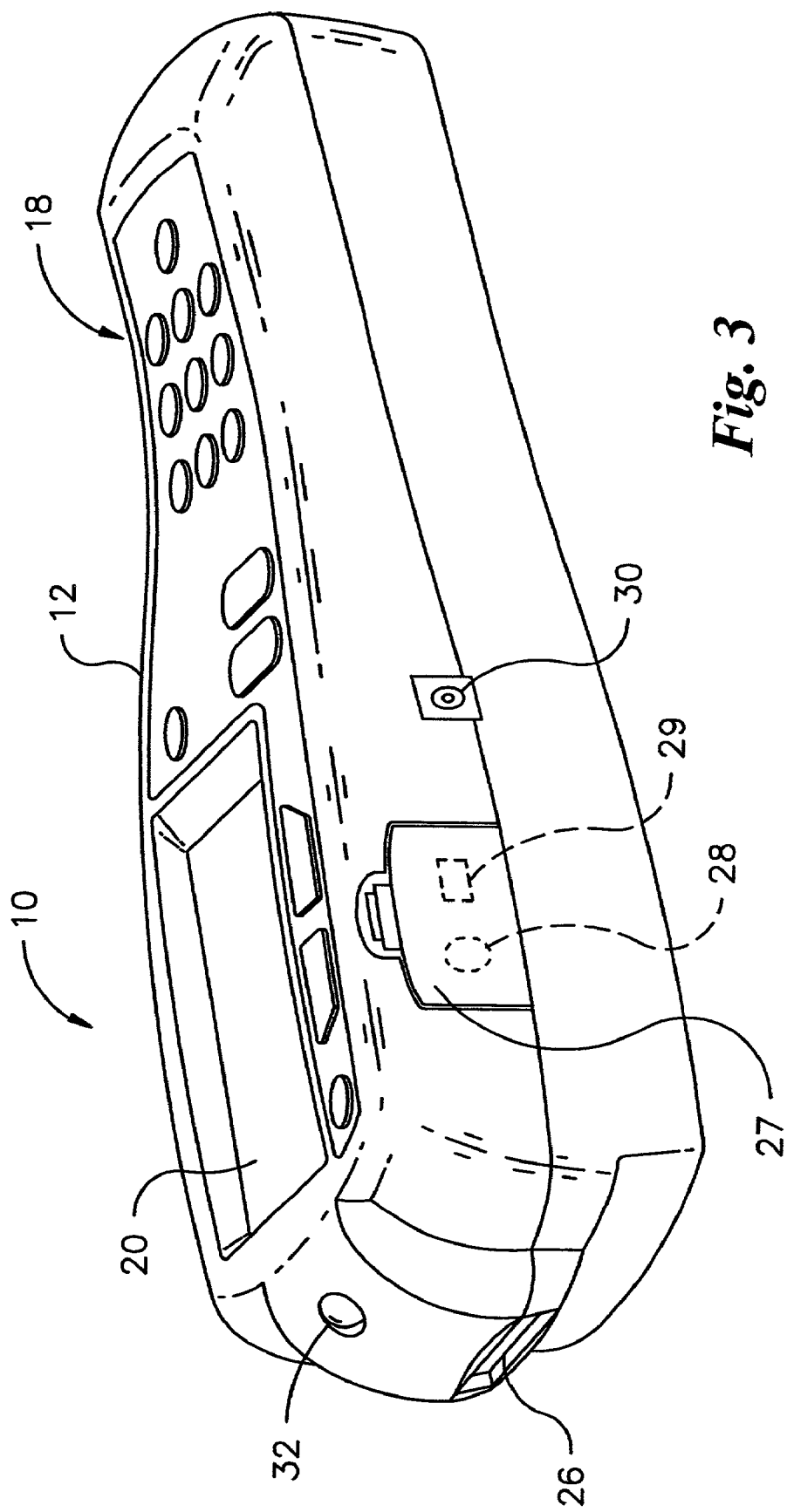

MEDICAL DIAGNOSTIC SYSTEM

CROSS-REFERENCE TO RELATED APPLICATIONS

This patent application claims the benefit of U.S. Provisional Patent Application No. 60/188,115, filed Mar. 9, 2000 entitled, "Medical Diagnostic System" and U.S. Provisional Patent Application No. 60/219,357, filed Jul. 19, 2000, entitled, "Medical Diagnostic System" the subject matter of each application being hereby incorporated herein by reference.

BACKGROUND OF THE INVENTION

The present invention relates generally to medical diagnostic systems and, more particularly, to a self contained hand-held portable instrument and an associated disposable sample container or test cell for performing a variety of real time medical diagnostic tests with respect to blood or other fluids received from humans or animals.

Electronic devices for automatically conducting a medical diagnostic test a utilizing a patient's blood or other bodily fluids in a laboratory, hospital or physician's office are generally well known. With such electronic devices, a small sample of the patient's blood or other bodily fluid is obtained by a health care professional for the purpose of conducting the analysis. In some such devices the blood or other bodily fluid is mixed with a dry or lyophilized activation reagent that is effectively re-hydrated when mixed with the blood or other fluid. The resulting fluid is then exposed to light at a particular wavelength and a photo detector receives the light signal reflected from the fluid to provide a resulting output diagnostic. Other such electronic devices function in the same, similar or different ways to obtain the desired result.

While such other prior art electronic diagnostic devices are generally effective in performing such medical diagnostic testing, such devices are often bulky and, therefore, are basically restricted to being used only in a laboratory or hospital or, in some cases, a physician's office. More recently, light weight portable devices have been developed for performing a limited number of certain individual or specific diagnostic tests. However, such more recent devices also suffer from defects including, in some cases, the ability to perform only a single diagnostic test or a single group of closely related diagnostic tests. In addition, some such more recent portable devices are structurally and/or functionally complex and relatively expensive to obtain and use. There thus exists a need for a relatively low cost, hand held, portable, self contained instrument which is capable of performing a plurality of different medical diagnostic tests with respect to individual samples of a patient's blood or other bodily fluid which is relatively inexpensive to obtain, simple and inexpensive to operate and yet, which provides an effective, consistent diagnostic quality result.

The present invention overcomes these and other problems associated with such prior art devices by providing a self contained medical diagnostic device and system which is small enough to fit in the palm of the hand of a user, but yet is programmed to perform a plurality of different medical diagnostic tests, including tests for glucose, calcium, potassium, lead, hematacrit, blood urea/nitrogen, creatinine, bilirubin, ALK phosphates and other such tests. The device and system of the present invention is also adaptable to perform standard medical urine chemistry tests and urinalysis, at least to the degree of accuracy necessary for adequate screening of controlled substances, as well as blood alcohol testing with an accuracy efficient for law enforcement use. The present medical device and system provides on the spot analysis in a very short time, usually a few minutes or less, and the results of the analysis is stored within the memory of the device for later downloading or other retrieval which improves efficiency and reduces manual record keeping. The accuracy of the results obtained using the present device/system is unaffected by the medical training, laboratory skills or lack of laboratory skills of the user. In using a device or system in accordance with the present invention, blood or some other bodily fluid is deposited into a special sample container or test cell by capillary action or a self-contained collection probe to facilitate real time reading of the results with little or no possibility of contamination due to delay, transport or the like. Because only a small amount of blood or other fluid is needed for the testing and analysis, a "finger stick" technique can sometimes be used resulting in less patient apprehension or discomfort. The analysis occurs substantially, immediately (typically within one to three minutes) resulting in little or no sample deterioration, which often occurs when samples are transported to a remotely located laboratory or other facility for analysis. A device or system in accordance with the present invention employs a special registration technique, in a preferred embodiment, using special barcoding to insure that the device or system performs the appropriate diagnostic test for the particular test cell and that the results of the test are properly stored in a manner which precludes the possibility of transposing the test results from different patients.

BRIEF SUMMARY OF THE INVENTION

Briefly stated, in one embodiment, the present invention comprises a system for conducting a plurality of different medical diagnostic tests. The system comprises a hand-held portable, self-contained electronic instrument for engaging a disposable test cell containing a fluid to be tested. The instrument performs a diagnostic test selected from the plurality of tests upon the fluid within the test cell with the test being selected by the instrument based upon identification information obtained from the test cell. A disposable, single use test cell is provided for receiving fluid to be diagnostically tested. The test cell includes identification information indicative of a particular diagnostic test to be performed upon the fluid contained therein. The test cell is also sized and shaped for engagement by the instrument.

In another embodiment, the present invention comprises a disposable, single use test cell for receiving a fluid to be diagnostically tested by an instrument. The test cell comprises a housing sized and shaped for engagement by the instrument when a diagnostic test is to be performed. The housing includes at least one chamber, a first bore in fluid communication with the at least one chamber and a second bore in communication with the at least one chamber. A pair of electrodes are located within the at least one chamber for performing ion selective analysis. The electrodes are in electrical contact with circuitry within the instrument when the housing is engaged by the instrument. A calibration capsule is located within the first bore. The calibration capsule contains calibration fluid for calibrating the electrodes. A specimen capsule is located within the second bore. The specimen capsule contains the fluid to be tested. Calibration fluid from the calibration capsule flows from the first bore to the at least one chamber for calibration of the electrodes and the fluid to be tested flows from the specimen capsule to the second bore to the at least one chamber for analysis by the electrodes.

BRIEF DESCRIPTION OF THE SEVERAL VIEWS OF THE DRAWINGS

The following detailed description of preferred embodiments of the invention will be better understood when read in conjunction with the appended drawings. For the purpose of illustrating the invention there are shown in the drawings embodiments which are presently preferred. It should be understood, however, that the invention is not limited to the precise arrangements and instrumentalities shown. In the drawings:

FIG. 1 is a top plan view of a medical diagnostic instrument in accordance with a preferred embodiment of the present invention;

FIG. 2 is a right side elevational view of the instrument shown in FIG. 1;

FIG. 3 is a left side perspective view of the instrument shown in FIG. 1;

DETAILED DESCRIPTION OF THE INVENTION

Figure 4A:
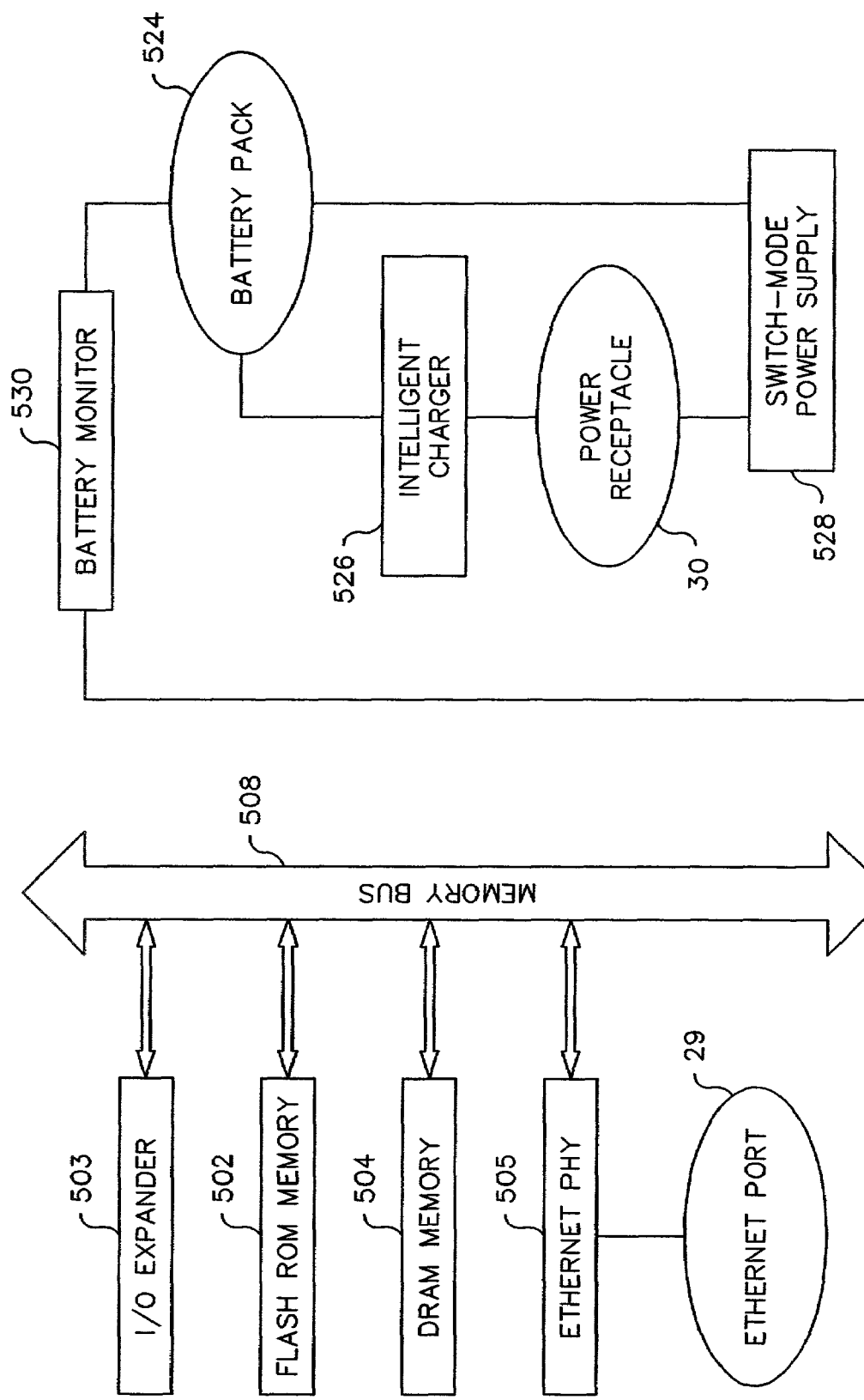
FIGS. 4A and 4B (collectively referred to as FIG. 4) are a functional schematic block diagram of the electrical/electronic and related components of the instrument shown in FIG. 1.

The present invention comprises a hand-held portable self contained instrument and system for performing medical diagnostic testing utilizing blood or other fluid from a patient. FIGS. 1–3 show a first preferred embodiment of a medical instrument or device 10 in accordance with the present invention. As best shown in FIG. 1, the instrument 10 is comprised of a housing 12 which is preferably formed of a generally rigid, preferably polymeric material, such as polyvinyl chloride or some other such polymeric material well known to those of ordinary skill in the art. The device 10 includes a keyboard on the front panel 17 which contains a plurality of actuators or keys, including a power on/off key 13, a scan key 14, a cancel key 15, an enter key 16 and ten alphanumeric keys 18. The keys 13, 14, 15, 16 and 18 are employed for permitting a user to communicate with the instrument 10 as with other hand-held instruments and in a manner which will hereinafter become apparent. The device 10 also includes a display 20, in the present embodiment a standard alphanumeric/graphics mode liquid crystal display of a type well known to those of ordinary skill in the art. The display 20 is employed for providing instructions to a user, displaying menus to facilitate operation of the device 10 and for providing information and/or data to a user concerning the status or results of a particular diagnostic test being performed. In the present embodiment the LCD display 20 is a color LCD model DMF-51161NCU-FW-AA from Optrex which uses passive color technology and a white cold cathode fluorescent lamp as a backlight. However, it will be apparent to those skilled in the art that some other LCD or other type of display from the same or some other manufacturer could alternatively be employed in the instrument 10. Preferably, the LCD display 20 is a 240×160 pixel display, but a display of some other size could be used if desired. The housing 12 further includes a pair of actuator buttons 22 and 24, which permit manipulation and/or selection of the menus and other information or data displayed on the LCD display 20.

Referring now to FIG. 3, the instrument 10 also includes a printer (not shown) which is located within the housing 12 to provide a printed output on paper or some other media. The housing 12 includes a suitable elongated slot 26 to facilitate removal of printed paper. The printer is preferably a compact thermal printer as will hereinafter be described in greater detail. The printer is adapted to print a variety of information, including patient identification information, date and time of the performance of a test, calibration information, test results and the like, including gray-scale pictures and graphics.

As also shown in FIG. 3, the instrument 10 also includes a removable cover 27 which encloses output ports including an RS 232 interface 28 for interfacing/downloading/uploading test or other data to either a local or remotely located computer (not shown) and/or for receiving software updates, data or the like from a local or remotely located computer (not shown). The instrument 10 further includes an Ethernet port 29 for connection to a local area network, local or remotely located computer or other external hardware, generally at a faster rate than the RS 232 port. The structure and operation of the RS 232 interface 28 and the ethernet port 29 are well known to those of ordinary skill in the art and need not be described in greater detail for a full understanding of the present invention. A battery charger connection 30 is also provided.

The instrument 10 also includes a scanner 32 for scanning information into the device 10 in a manner which will hereinafter be described. Information which may be scanned in includes patient identification information, information to identify a particular diagnostic test to be performed, information concerning the identity of a particular test cell, as well as other information. In the present embodiment, the scanner 32 is a standard, laser scanning barcode reader of the type well known to those of ordinary skill in the art. However, it will be apparent by those of ordinary skill in the art that some other type of scanner or scanning device could alternatively be employed for providing the information to the device 10. Alternatively, if desired, a coding scheme other than a standard barcode could be employed for entry of the information into the instrument 10. Barcoded surfaces are held in the path of a laser beam of the scanner 32 for reading the barcode.

As best shown in FIG. 2, the instrument 10 further includes a slot-like opening 34 on the right side thereof. The opening 34 includes a generally elongated rectangularly shaped portion 36 with generally semi-circular shaped portions 38 on each end, which together function as a keyway to facilitate the introduction of a sample container or test cell 300 into the housing 12 with a particular orientation. As will hereinafter become apparent, the test cell 300 is employed for collecting and introducing the blood or other fluid from a patient into the instrument 10 for the purpose of performing the selected diagnostic test. It will be appreciated by those of ordinary skill in the art that the size and shape of the slot-like opening 34 may vary from what is shown and described for a particular application. Of course, the slot-like opening 34 must compliment or conform to the size and shape of the test cell 300.

As discussed above, the instrument 10 is contained within a unitary housing 12, which also contains a power source (not shown in FIGS. 1–3) and all of the electrical and electronic components, circuitry and software (not shown in FIGS. 1–3) necessary to permit the instrument 10, by itself, to perform the necessary diagnostic testing upon a fluid sample within an installed test cell 300. Preferably, the power source comprises one or more rechargeable batteries to facilitate stand alone operation of the instrument 10.

Figure 4B:
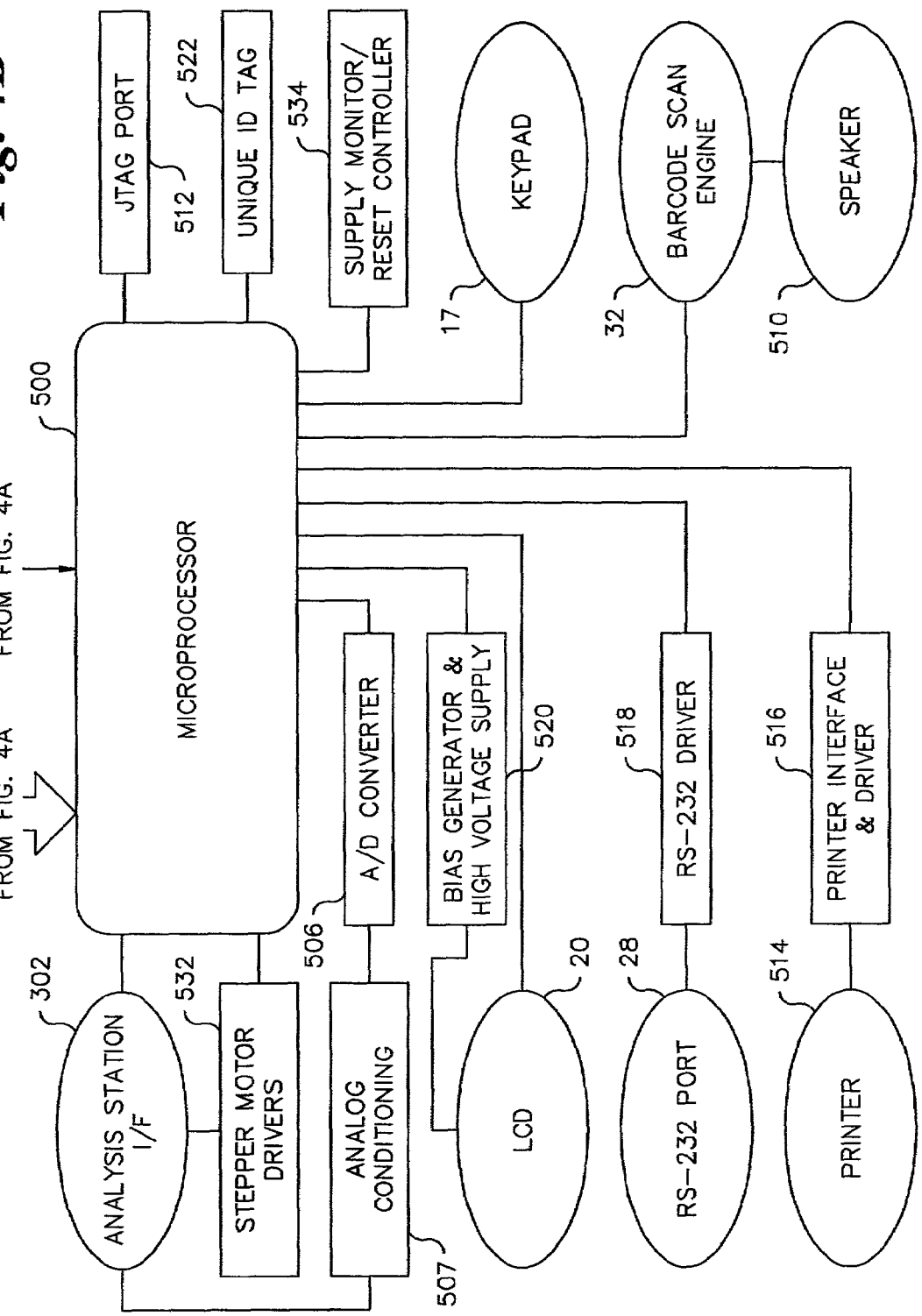

In the presently preferred embodiment, the instrument 10 performs a desired medical diagnostic test upon blood or other fluid removed from a patient by reading/measuring certain calibrated electrical characteristics of the blood or other fluid from the patient, comparing the measured electrical characteristics to a set of previously stored values and reaching a conclusion based upon the result of the comparison. The instrument 10 is capable of performing potentiometric, amperometric and conductometric electrochemical tests and test cells designed for each type of test are used. FIG. 4 (which comprises FIGS. 4A and 4B viewed together) is a functional schematic hardware block diagram of the electrical/electronic and other related components of the preferred embodiment of the instrument 10. It should be appreciated by those of ordinary skill in the art that the various electrical/electronic components and the functions presented in FIG. 4, which will hereinafter be described in greater detail, are merely one illustration of the electrical/electronic workings of a preferred embodiment of the present invention. Thus, it should be clearly understood that other components may be substituted for any of the components shown on FIG. 4 and that components which perform other functions may alternatively be employed. In other words, the present invention is not limited to the precise structure and operation of the electrical/electronic and related components shown in FIG. 4 and as will hereinafter be described.

Referring now to FIG. 4, the heart of the instrument 10 is a processor or microprocessor 500. In the presently preferred embodiment, the microprocessor 500 is an advanced RISC machine (ARM) architecture with a built-in memory bus controller, real time clock and liquid crystal display (LCD) controller and a series of at least four serial interface ports. Additional user-defined, general purpose input/output (I/O) pins or ports are provided for connection of additional peripheral devices as hereinafter described. The clock speed, which preferably is software programmable, is preferably set to be at about 59 MHz, in order to provide enhanced power efficiency. The processor core operates on a 1.5V power supply, while the real-time clock and most input/output functions operate on a 3.3V power supply. In the presently preferred embodiment, the microprocessor 500 is an Intel SA-1110 StrongARM microprocessor, however, it will be apparent to those of ordinary skill in the art that a different Intel microprocessor or a microprocessor from a different manufacture may alternatively be employed.

The instrument 10 further includes a flash read only memory (ROM) 502, a dynamic random access memory (DRAM) 504, a general purpose input/output expander 503 and an ethernet PHY interface 505 each of which access and are accessed by the microprocessor 500 by the memory bus 508 in a manner well known in the art. In the present embodiment, there are four megabytes of flash ROM 502 and four megabytes of DRAM 504. The DRAM 504 is provided by a pair of ISSI (Integrated Silicon Solutions, Inc.) Model IS41LV16100 integrated circuits each organized as 1 Mbit×16 bits. The DRAM 504 supports the software operating within the processor 500. The flash ROM 502 is preferably an Intel RC8F320J3-100 strata flash memory integrated circuit and is responsible for retaining all system software and all patient records, even when power is removed and facilitating the upgrading of system software without having to add or replace any memory components. Different chips from the same or different manufacturers may alternatively be used for the Flash ROM 502 and/or the DRAM 504 if desired.

The input/output expander 503 provides additional general purpose input/output connections to other devices within the instrument 10. The input/output expander 503 is a SN74AC373, 16 bit latch circuit from Texas Instruments. The ethernet PHY interface 505 is a Model CS8900A-CQ3 integrated circuit from Cirrus Logic and provides for a 10 megabit per second connection to a local area network, computer or other external device. The ethernet PHY interface circuit negotiates between the connected external device and the microprocessor 500 via the memory bus 508. The ethernet PHY interface 505 includes a PHY integrated circuit, isolation magnetics and required support elements and provides for a connection which is much faster (approximate 1000 times faster) than the standard RS 232 port 28 can provide. Different components from the same or different manufacturer may be used for the input/output expander 503 and/or the ethernet PHY interface 505 if desired.

The microprocessor 500 controls the system power supply as hereinafter described and enters a sleep mode whenever the instrument 10 is powered off. At that time, most internal microprocessor functions are halted, the main power supply is shut down and the real time clock is kept running to maintain the correct date and time of day. The sleep mode is exited by the instrument 10 sensing the depressing of any of the keys 13, 14, 15, 16 or 18. In the event that all power to the instrument 10 is removed such as when the batteries are replaced, a reset controller within the microprocessor 500 issues a reset signal upon the restoration of power to clear the real time clock so that the software and the user are aware that all power was lost. The ability of the microprocessor 500 to write to the Flash ROM 502 is inhibited whenever the power is being removed or restored to the instrument 10 until after the power supply and the microprocessor 500 stabilize to prevent the accidental altering of the contents of flash ROM 502 when power is cycling.

A first serial port of the microprocessor 500 is used for a direct connection to the barcode scanner 32. In the present embodiment, a swept laser beam style barcode reader based upon a Symbol Technologies Model SE-923-1000A is employed as the barcode scanner 32. The scanner 32 is a self contained unit that transmits a swept laser beam onto a target barcode label and recovers the reflected label information which is decoded and sent to the microprocessor 500 through the first serial port. The scan engine within the scanner 32 also drives an external sounding element or speaker 510 to provide a chirp, beep or other sounds as feedback to a user for confirmation of a valid barcode read.

A second serial port is used for connecting the microprocessor 500 to a printer 514. In the present embodiment, the printer 514 is preferably a compact thermal printer mechanism which has been selected for its quietness, efficiency and ease of connection to the microprocessor 500. In the present embodiment the printer 514 is a Panasonic Model EPL 2001.52 printer with a separate controller. Other printers of other types or from other manufacturers may be used if desired. Preferably, the printer 514 is software addressable and is capable of providing good resolution greyscale pictures and graphics. Printer control and driver circuitry 516 is provided to manage operation of the printer 514 and to provide a suitable interface to the microprocessor 500. In the present embodiment the printer control and driver circuitry 516 is a companion integrated circuit Model Number EPL SAR2001 from Panasonic. Other circuitry may alternatively be employed.

A third serial input/output port of the microprocessor 500 is used to provide the RS 232 communication port 28 to serve as an interface for a locally located or remotely located host computer or to an external modem connection for dial out capability. Preferably, the port 28 is linked to the serial port of the microprocessor 500 through a RS 232 driver circuit 518 to provide electrostatic discharge isolation and proper signaling levels for external communication to and from the instrument 10. The RS 232 driver circuit 518 in the present embodiment is a Linear Technology LT1342CG RS 232 driver IC. Other driver circuitry from other manufacturers could be used if desired. The external connection 28 may be used for retrieval and installation of upgraded operating software, transmission of patient records to remote locations, downloading patient information and uploading of patient records to a host computer.

A fourth serial input/output port of the microprocessor 500 is used for receiving data from an analysis station 302 which will hereinafter be described in greater detail. The analysis station 302 is capable of performing at least three general types of electrochemical tests on blood or some other fluid obtained from a subject to be tested. The three general types of electrochemical tests are potentiometric, amperometric and conductometric. Analog signals obtained from the analysis station 302 as a result of readings taken during the conducting of a test are initially conditioned by analog conditioning circuitry 507 and are then fed to an analog to a digital (A/D) converter 506, the output of which is connected to the microprocessor 500 through the fourth serial input/output port. The analog to digital convertor 506 in the present embodiment is a Texas Instruments TLV2548 integrated circuit. However, other suitable A/D convertors from the same or other manufacturer may be employed if desired. The A/D convertor 506 receives analog voltage signals from the analog conditioning circuitry 507 and converts the signals to digital signals which are sent to the microprocessor 500.

As will hereinafter be described the analysis station 302 employs stepper motors (linear actuators) and position sensing microswitches for performance of the electrochemical diagnostic tests as will hereinafter be described. The stepper motors are controlled by the microprocessor 500 using stepper motor drivers 532, which control the linear movement of the stepper motors or linear actuators. The stepper motor drivers 532 are connected to a general purpose input/output pin/port of the microprocessor 500 and to the stepper motors or linear actuators within the analysis station 302. The position sensing microswitches are also connected to the microprocessor 500 through the stepper motor drivers 532. In the present embodiment, the stepper motor drivers 532 comprise a ROM BA6845FS stepper motor driver, although, it will be apparent to those of ordinary skill in the art that other stepper motor drivers from other manufactures may alternatively be used.

As previously mentioned, the microprocessor 500 preferably includes a graphics mode liquid crystal display controller, so that no external controller is needed to interface to the LCD graphic display 20. The graphic LCD display 20 is connected to a general purpose input/output pin/port of the microprocessor 500 and is preferably arranged as 240×160 pixels with a 0.24 mm. pitch. The LCD display 20 preferably includes on board drive circuitry that interfaces directly to a general purpose input/output pin/port of the processor 500 via standard data and control signals. The built in LCD controller of the microprocessor 500 is responsible for generating the required signaling format for the LCD display 20. Preferably, the LCD display 20 uses a while cold cathode fluorescent back lighting arrangement, which is controlled by the microprocessor 500. A separate bias generator and high voltage supply 520 is provided to generate the DC bias for operation of the LCD display 20 and the high voltage needed for the backlight.

Another general purpose input/output pin/port of the microprocessor 500 is connected to a unique identification tag circuit 522. The unique identification tag circuit 522, includes a Dallas Semiconductor integrated circuit #DS2401 or other component, which establishes a unique identification code, like a digital serial number for the particular instrument 10. The unique identification code is used in connection with test results and other data to permit positive, unique identification of the particular instrument 10, which provided the test result. Thus, each instrument 10 includes a unique identification code to provide positive identification of all test results obtained using the instrument 10.

Four dedicated input/output pins/ports of the microprocessor 500 are connected to a standard JTAG port 512. The JTAG port 512 is used to enhance testing during manufacturing of the instrument 10 and to facilitate the initial installation and post assembly updating and authentication of firmware/software. Another three input/output pins/ports of the microprocessor 500 are connected to the various actuators or keys on the front panel 17 of the instrument 10. A Supply Monitor/Reset Controller 534 is connected to the reset input pin of the microprocessor 500. In the present embodiment, the supply monitor/reset controller 534 is a series of components which together monitor various voltages on the circuit board (not shown) which supports the above-identified electrical/electronic circuitry and effectively shuts down the microprocessor 500 by issuing a hard reset signal whenever one or more of the monitored voltages falls outside of a prescribed range. The result is that any ongoing diagnostic tests are aborted and no new tests may be performed until the correct voltage levels are restored and the microprocessor 500 is again operative.

The main source of power for the instrument 10 is a battery pack 524. In the present embodiment, the battery pack 524 is comprised of six (6) series connected nickel-metal hydrid (NiMH) batteries to provide a nominal 7.2 volt output source. The use of nickel-metal hydrid technology allows for high energy density and quick recharge times. However, other types of batteries such as nickel-cadmium (NiCD) and lithium-Ion (LiIon) and others known to those skilled in the art could be used. The instrument 10 also includes an intelligent fast charge controller 526 which functions to recharge the battery pack 524, typically in two hours or less and continuously monitors battery temperature using a sensor (not shown) embedded within the battery pack. In the present embodiment, the intelligent battery charger comprises a Maxim MAX 712 integrated circuit. Other intelligent battery charger circuits may be used if desired. If the battery pack temperature is to high or too low, the intelligent charger 526 stops the fast charging operation until a safe battery pack temperature level is reached. A self resetting fuse (not shown) is also embedded within the battery pack 524 to provide enhanced safety. The battery charger 526 is activated whenever an accompanying AC adapter wall pack (not shown) is connected to the instrument 10 through the battery charger connection 30 (FIG. 3) to provide power to the instrument 10 and to permit normal use of the device 10 during recharging of the battery pack 524. A second fuse (not shown) is also provided at the input connection for the wall pack and both the battery pack 524 and the wall pack connections have reverse polarity protection.

The instrument 10 requires several regulated voltages to properly function. The various voltages are provided by a switch-mode power supply 528 which includes a dual phase switching regulator. In the present embodiment a Linear Technology LTC 1628 switch mode integrated circuit is used, but some other circuit from another manufacturer could alternatively be used if desired. A control integrated circuit of the regulator provides 5V and 3.3V standby outputs which are always active for providing power to the real time clock of the processor 500 and to a battery monitor circuit 530. In the present embodiment, the battery monitor circuit 530 includes a Texas Instruments BQ2010SN battery monitor integrated circuit. Other circuitry from other manufacturers may alternatively be employed in a particular application. The battery monitor circuit 530 continually measures current flow into and out of the battery pack 524 to determine the current state of charge of the battery pack 524. The battery monitor circuit 530 also estimates internal battery loss when no current is flowing based upon time and temperature. The battery monitor circuit 530 communicates with the microprocessor 500 via a one wire serial interface. It will be appreciated by those of ordinary skill in the art that while a particular battery pack/power supply arrangement has been described, the present invention is not limited to a particular battery pack, power supply, charger or battery monitor.

Referring now to FIGS. 5–8, there is shown a preferred embodiment of a first disposable, single use test cell 300 for use within the above-identified instrument 10 in accordance with the present invention. The test cell 300 is employed for receiving a small quantity of blood or other fluid from a patient or other subject of a diagnostic test to be performed and for thereafter being inserted into the instrument 10 for the performance of the selected diagnostic test. Each test cell 300 contains all of the necessary reagents, calibrates, sensors and the like for the performance of a single diagnostic test.

The present embodiment further includes an analysis station 302 (FIGS. 9–11) located within the instrument 10 for receiving the test cell 300 in a manner which will hereinafter be described. The analysis station 302 functions as the mechanical and electrical interface between the microprocessor 500 and a test cell 300, which has been received in the slot-like opening 34 of the instrument housing 12 as shown in FIG. 1. It should be appreciated by those of ordinary skill in the art that the precise structure of the first test cell 300 and/or the analysis station 302 as shown in FIGS. 5–11 and as hereinafter described in detail are merely that of a currently preferred embodiment and that variations may be made to the structure of either the test cell 300 or the analysis station 302 without departing from the scope and spirit of the invention. Thus, the present invention is not limited to the precise structure of the test cell 300 or the analysis station 302 as shown and hereinafter described, but is intended to encompass structural and/or operational variations as well as other test cells and analysis stations which perform the same, or substantially the same functions, as those of the test cell 300 and analysis station 302 as hereinafter described.

Figure 5:
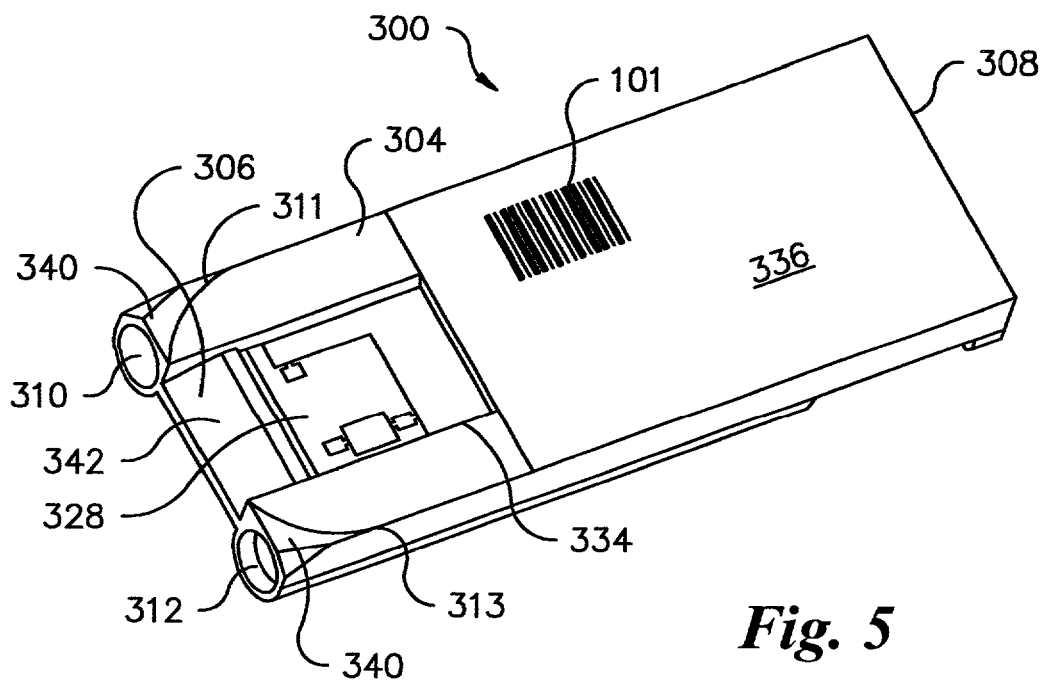
FIG. 5 is a top perspective view of a first preferred embodiment of a test cell in accordance with the present invention.
Figure 6:
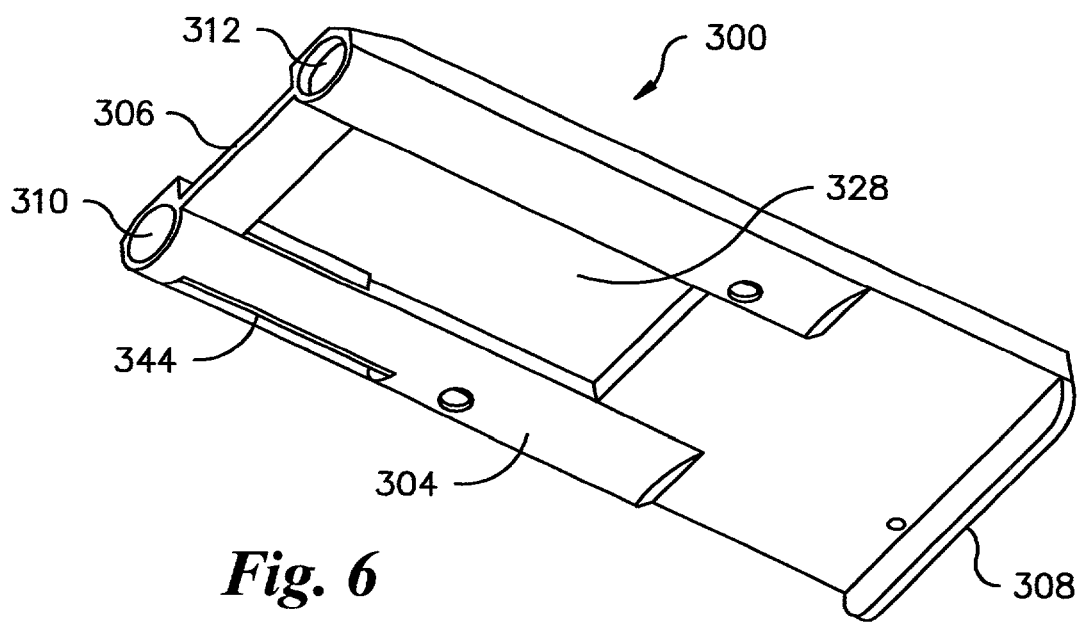
FIG. 6 is a bottom perspective view of the test cell shown in FIG. 5.
Figure 7:
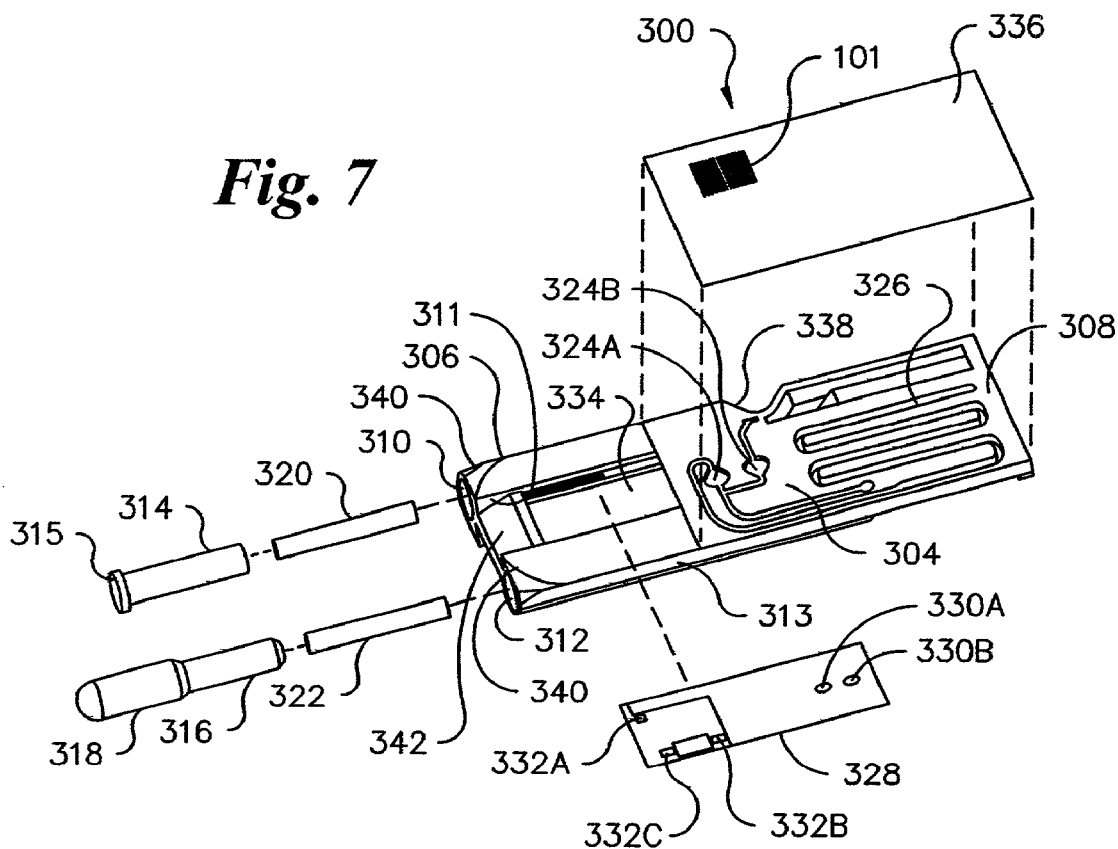
FIG. 7 is an exploded perspective view of the test cell shown in FIG. 5.

As best shown in FIGS. 5–7, the test cell 300 is comprised of a generally elongated, generally rectangular housing 304 having a first or insertion end 306 and a second or gripping end 308. The insertion end 306 includes a pair of generally parallel spaced bores 310, 312 extending within corresponding generally cylindrically shaped portions 311, 313 which are open on the insertion end 306 for receiving respectively therein a calibration capsule 314 and a specimen capsule 316. The calibration capsule 314 contains a supply of calibration fluid of a specific type used for the particular diagnostic test to be performed. Thus, a separate test cell 300 with specially chosen electrical contacts, chambers and chemicals (calibration fluid and/or electrolyte) is employed for each diagnostic test. The calibration capsule 314 is generally cylindrical and is preferably formed of a polymeric material, such as medical grade polypropylene. Other suitable materials may alternatively be employed. The specimen capsule 316 is of the pipet type and includes a squeezeable portion 318 on one end which is employed for sucking in or pushing out a sample of the blood or other fluid of a subject upon whom a diagnostic test is being performed. A pair of elongated tubes 320, 322 are provided within the bores 310, 312 for receiving, sealing and engaging the interiors of the calibration capsule 314 and specimen capsule 316 respectively to provide fluid communication with the remainder of the test cell housing 304, as will hereinafter be described. Preferably, the calibration capsule 314 is filled with the appropriate calibration fluid for a selected diagnostic test to be conducted using the test cell 300 and is initially installed within bore 310 at the time the test cell 300 is manufactured. Preferably, the specimen capsule 316 is not initially fully installed in the bore 312 of the test cell housing 304. Instead, the specimen capsule 316 may be easily removed from the bore 312 or is initially kept separate to facilitate pipeting or sucking of the blood or other fluid into the specimen capsule 316 by squeezing and then releasing the squeezable portion 318 while the other, open end engages the blood or other fluid. Once the blood or other fluid is drawn into the specimen capsule 316, the specimen capsule 316 is inserted into the bore 312 of the test cell housing 304 with the tube 322 engaging and sealing the interior of the specimen capsule 316 and with the squeezable portion 318 extending at least slightly outwardly from the insertion end 306 of the test cell housing 304. The bore 312 establishes when the specimen capsule 316 is properly inserted.

The test cell housing 304 includes a pair of generally circular electrode chambers 324A and 324B which are in fluid communication (by small fluid passageways) with one or both of the bores 310, 312. The electrode chambers 324A and 324B are also in fluid communication (through a separate fluid passageway) with an overflow chamber, which in the present embodiment is in the form of a serpentine passageway 326 located proximate to the gripping end 308 of the test cell housing 304. The serpentine passageway 326 is employed for receiving excess blood or other bodily fluid and/or excess calibration fluid, which overflows from or otherwise flows out of the electrode chambers 324A and 324B. An electrode/contact pad assembly 328 is secured to the bottom or undersurface of the test cell housing 304. The electrode/contact pad assembly 328 includes a pair of electrodes 330A and 330B which, when the electrode/contact pad assembly 328 is suitably installed, extend into the respective electrode chambers 324A and 324B. The test cell 300, in the present embodiment, employs ion selective technology for performing the various diagnostic tests, a technique known in the diagnostic testing art and well adapted for use in a hand held instrument 10. For this purpose an ion selective electrode 330A is used with a reference electrode 330B. The electrodes 330A and 330B are generally circular and are preferably made of a conductive material, such as silver/silver chloride, graphite, platinum or the like, which is secured to a substrate 329. The substrate 329 is partially covered by a dielectric layer 331 with two aligned circular openings 333 each being slightly smaller in diameter than the diameter of the electrodes 330A and 330B. The openings 333 extend through the dielectric layer 331 to establish small generally circular wells for receiving an ion selective membrane, electrolyte, gel or other electrochemically responsive material (not shown), which covers each electrode 330A, 330B. Preferably the thickness of the dielectric layer 331 and the size of the openings 333 combine to provide for an appropriate amount of electrolyte to be installed within each of the wells. The particular material which is installed within the wells depends upon the particular diagnostic test being performed. Preferably, at least part of the material is in the form of a gel impregnated with ionic material, such as sodium chloride, sodium nitrate or other materials of optimum ionic conductivity. However, the electrolyte could be in some other form, if desired. For example, a powder or a solid electrolyte such as Eastman AQ or Nafion could be used. As a further alternative a simple coated wire electrode CWE could be used. Once the electrolyte is inserted within the wells formed by the openings 333 within the dielectric layer 331, a covering of an ion selective membrane (not shown) is applied to seal at least one of the openings 333 and a permeable membrane (not shown) may or may not be added to seal the other of the openings 333. In the present embodiment, the membrane is made of polyvinylchloride (PVC), polyurethane or other suitable polymer which is impregnated or doped with a chemical species, the ionosphone selected for the diagnostic test to be performed. Alternatively, the membrane may be solid state for some diagnostic tests. It will be appreciated by those of ordinary skill in the art that a membrane made of other materials may alternatively be used.

When the electrode/contact pad assembly 328 is installed, the electrodes 330A, 330B extend into the bottom of the respective electrode chambers 324A, 324B with the covering membranes exposed to calibration fluid and blood or other fluids during the performance of a diagnostic test as will hereinafter be described. The electrode/contact pad assembly 328 further includes three electrical contacts 332A, 332B and 332C which, when the electrode electrode/contact pad assembly 328 is installed are accessible through a generally rectangular opening 334 between the cylindrical portions 311, 313 of the test cell housing 304. Two of the electrical contacts 332A and 332B are electrically connected to the electrodes 330A and 330B and are employed for establishing an electrical connection between the electrodes 330A and 330B and the electrical/electronic circuitry (shown in FIG. 4) within the instrument 10. The third electrical contact 332C is connected through a resistor 335 to the second contact 332B. The resistance value of the resistor 335 is selected depending upon the type of diagnostic test which is being performed by the instrument 10 utilizing a particular test cell 300. Each type of diagnostic test has an assigned resistance so that when a test cell 300 is inserted into the instrument 10, the resistance between contacts 332C and 332B is read and compared with an expected value stored in memory to confirm that the inserted test cell 300 corresponds to the particular diagnostic test to be performed. Further details concerning the manner in which the contacts 332A, 332B, 332C are employed will hereinafter be described.

A generally rectangular, generally flat cover 336 is secured to and covers the upper surface of at least the gripping end 308 of the test cell housing 304 to enclose the electrode chambers 324A and 324B, serpentine passageway 326 and interconnecting passageways. The outer surface of the cover 336 includes suitable identification indicia, including a barcode 101, which identifies the diagnostic test which may be performed using the particular test cell 300. Preferably, the test cell 300 is also color coded to correspond to a particular diagnostic test. Preferably, the test cell housing 304, electrode/contact pad assembly 328, tubes 320, 322, calibration capsule 314, specimen capsule 316 and cover 336 are all made of the same generally rigid polymeric material which is preferably a medical grade polyvinyl chloride (PVC). It will be apparent to those of ordinary skill in the art that other polymeric or nonpolymeric materials may alternatively be used for all or some of the above-described components of the test cell 300. Preferably, the test cell 300 is assembled and the various components are secured together utilizing a suitable medical grade or other adhesive or utilizing some other process, such as sonic welding or the like. Accordingly, it should be clearly understood by those of ordinary skill in the art that the present embodiment is not limited to a test cell 300 made of PVC nor is the present invention limited to such a test cell 300 which is assembled utilizing an adhesive.

For reasons which will hereinafter become apparent, the lateral sides of the test cell housing 304 are generally straight and flat. However, one of the lateral sides includes a generally arcuate notch or cutout portion 338, which is employed for securing the test cell 300 within the analysis station 302 in a manner which will hereinafter be described. Likewise, the upper portion of both lateral sides of the insertion end 306 of the test cell housing 304 includes a curved or beveled portion 340 to facilitate insertion of the test cell 300 into the analysis station 302 as will hereinafter be described. Similarly, the central portion of the insertion end 306 of the test cell housing 304 between the cylindrical portions 311, 313 includes a sloped or beveled portion 342 also for the purpose of facilitating insertion of the test cell 300 into the analysis station 302. Finally, the lateral side of the test cell housing 304 closest to the first bore 310 includes a longitudinally extending slot 344 for slidably receiving a portion of the analysis station 302 in a manner which will hereinafter be described.

Figure 9:
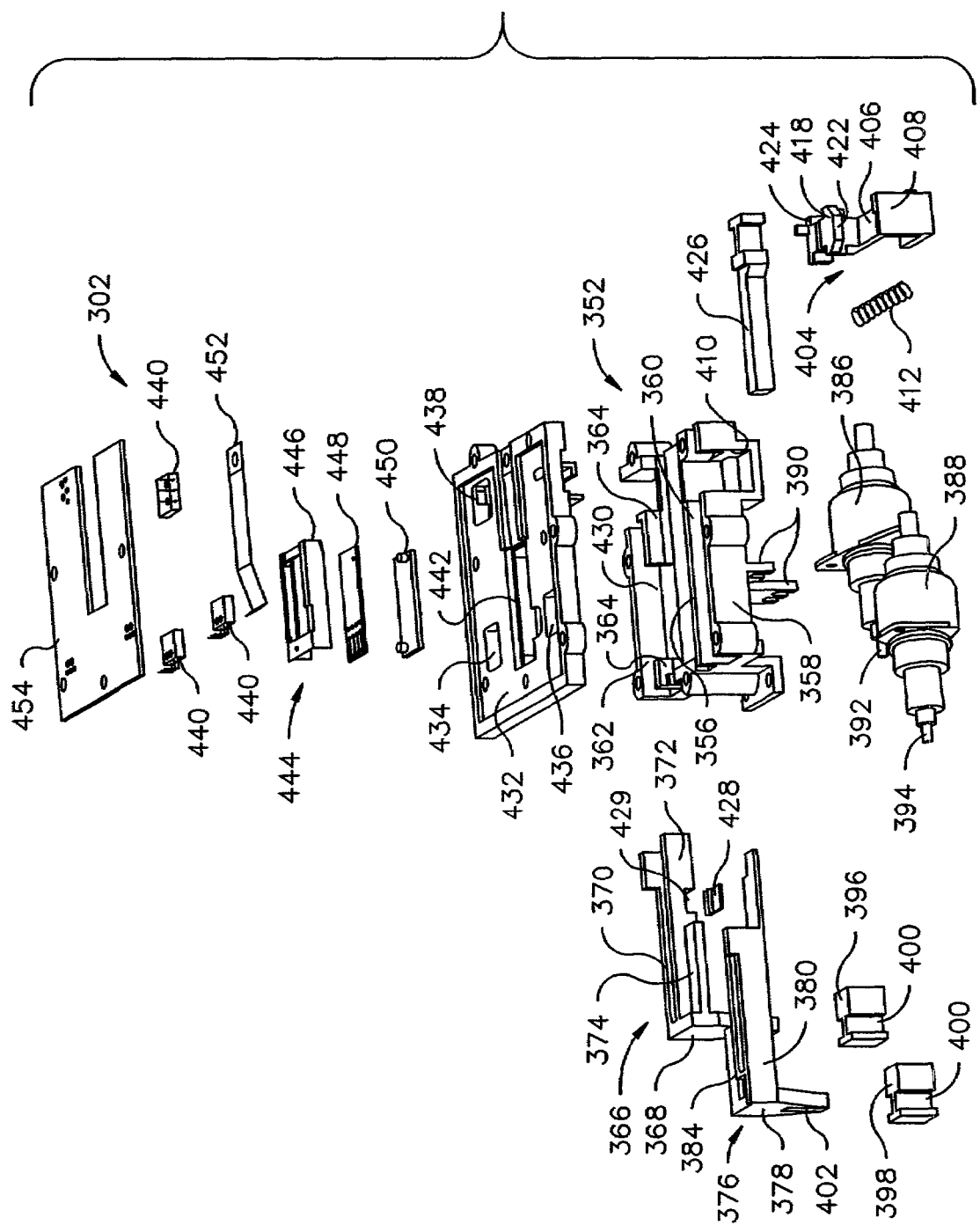
FIG. 9 is an exploded perspective view of an analysis station in accordance with a preferred embodiment of the present invention.
Figure 10:
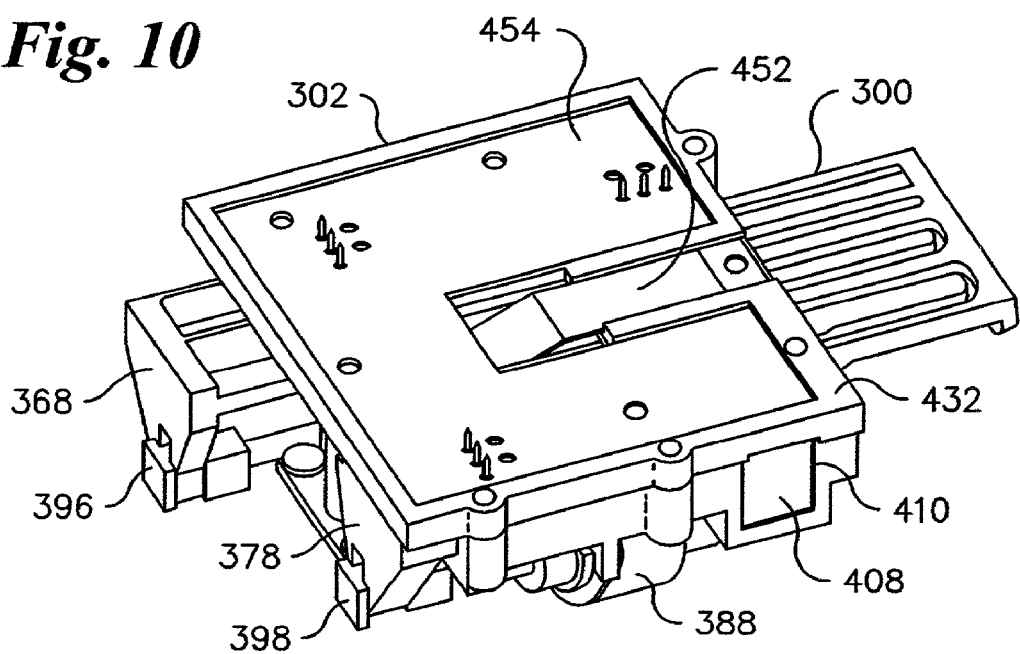
FIG. 10 is a top perspective view of the analysis station of FIG. 9.
Figure 11:
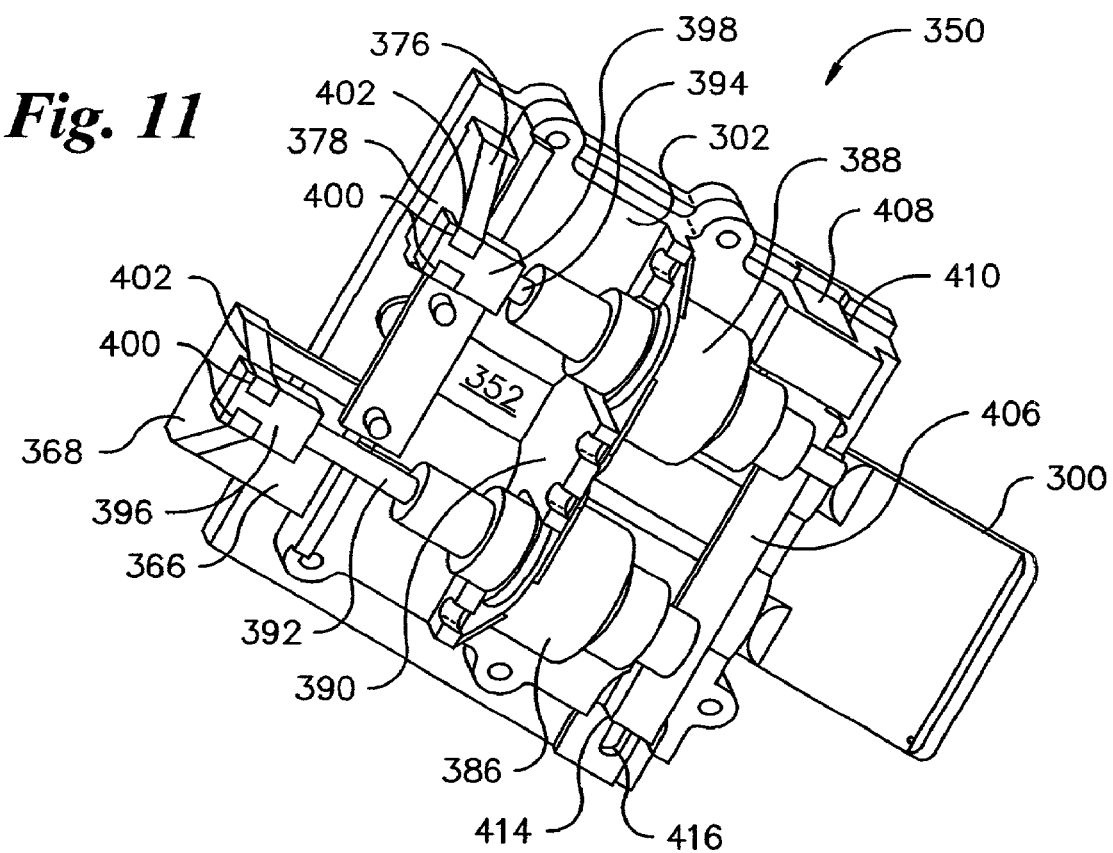
FIG. 11 is a bottom perspective view illustrating the components of the analysis station of FIG. 9.
Figure 12:
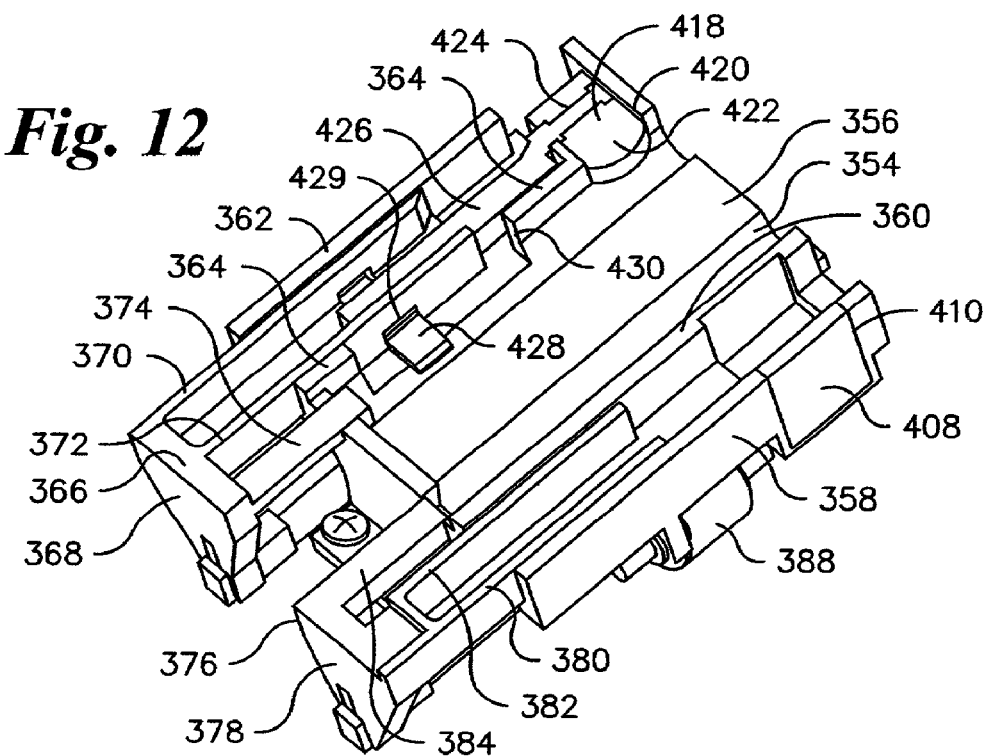
FIGS. 12–21 are top perspective views, partially, broken away, of the analysis station as shown in FIG. 9 with an inserted test cell for illustrating the stages involved in the insertion and removable of the test cell from the analysis station and the performance of a diagnostic test.

The analysis station 302 as shown in FIGS. 9–11 includes an irregularly shaped, but generally rectangularly shaped housing 350. The housing 350 includes a base portion 352 and a series of wall members or walls extending generally upwardly from the base portion 352. The walls include a relatively thick central wall 354 which includes a generally flat upper surface 356. The central wall 354 is sized and shaped for receiving the open area between the cylindrical portions 311, 313 of the test cell housing 304 which established the bores 310, 312, such that when the test cell 300 is inserted into the analysis station 302, the cylindrical portions 311, 313 straddle the central wall 354 and the undersurface of the test cell housing 304, particularly the electrode/contact pad assembly 328 is parallel to the flat upper surface 356 of the central wall 354. Two additional walls extend upwardly from the base portion 352 on each side of and generally parallel to the central wall 354 to establish on each side of the central wall 354 a guide path for receiving a linear slide member. More particularly, a second wall 358 extends upwardly from the lateral outer surface of the base portion 352 and a third wall 360 extends upwardly from the base portion 352 about halfway between the second wall 358 and the central wall 354. Similarly, a fourth wall 362 extends upwardly from the opposite lateral edge of the base portion 352 and a fifth wall 364 extends upwardly from the base portion 352, approximately midway between the fourth wall 362 and the central wall 354. Walls 362 and 364 cooperate with the central wall 354 to establish a pathway for a first elongated slide member 366. The first elongated slide member 366 is comprised of a generally vertically oriented base portion 368 and three generally parallel, elongated legs 370, 372, 374 extending generally outwardly therefrom. As best shown in FIG. 12, the first and second legs 370, 372 of the first elongated slide member 366 which are interconnected by a web portion therebetween extend into the area between the fourth wall 362 and the fifth wall 364 of the analysis station housing 350. The third leg 374 of the first slide member 366 extends into the area between the fifth wall 364 and the central wall 354 of the analysis station housing 350. In this manner, the first slide member 366 is adapted for sliding movement inwardly and outwardly with respect to the housing 350 as illustrated in FIGS. 12–18 and as will hereinafter be described in greater detail. A second elongated slide member 376 includes a vertical base portion 378 and three generally elongated generally parallel legs 380, 382, 384 extending generally perpendicularly therefrom. As best shown in FIG. 12, legs 380 and 382 of the second slide member 376 which are interconnected by a web portion extend into the area between the second wall 358 and the third wall 360 of the housing 350. Similarly, leg 384 of the second slide member 376 extends into the area between the third wall 360 and the central wall 354 of the housing 350. In this manner, the second slide member 376 may slide inwardly and outwardly with respect to the housing 350 as will hereinafter be described in greater detail.

As best shown in FIGS. 9 and 11, a pair of stepper motors or linear actuators 386, 388 are secured to the undersurface of the base portion 352 of the analysis station housing 350. Preferably, the linear actuators 386, 388 are electrical stepper motors and are secured to the base portion 352 utilizing suitable elongated fasteners, such as nuts and bolts (not shown), which extend through openings on a flange member 390 extending downwardly from the base portion 352 and through aligned openings in flanges extending outwardly from the linear actuators 386, 388. Each of the linear actuators 386, 388 includes an outwardly extending lead screw 392, 394, the distal ends of which are each secured to a brass tip member 396, 398 for concurrent movement therewith. Each of the tip members 390, 398 includes a pair of generally parallel grooves 400 on opposite sides thereof which receive and engage a slot 402 in the undersurface of the respective vertical base 368, 378 of the first and second slide members 366, 376 as best shown in FIG. 11. In this manner, the lead screws 392, 394 of each of the linear actuators 386, 388 are mechanically coupled to the respective first and second slide members 366, 376 to cause the slide members 366, 376 to move or slide longitudinally inwardly or outwardly with respect to the analysis station housing 350.

Figure 13:
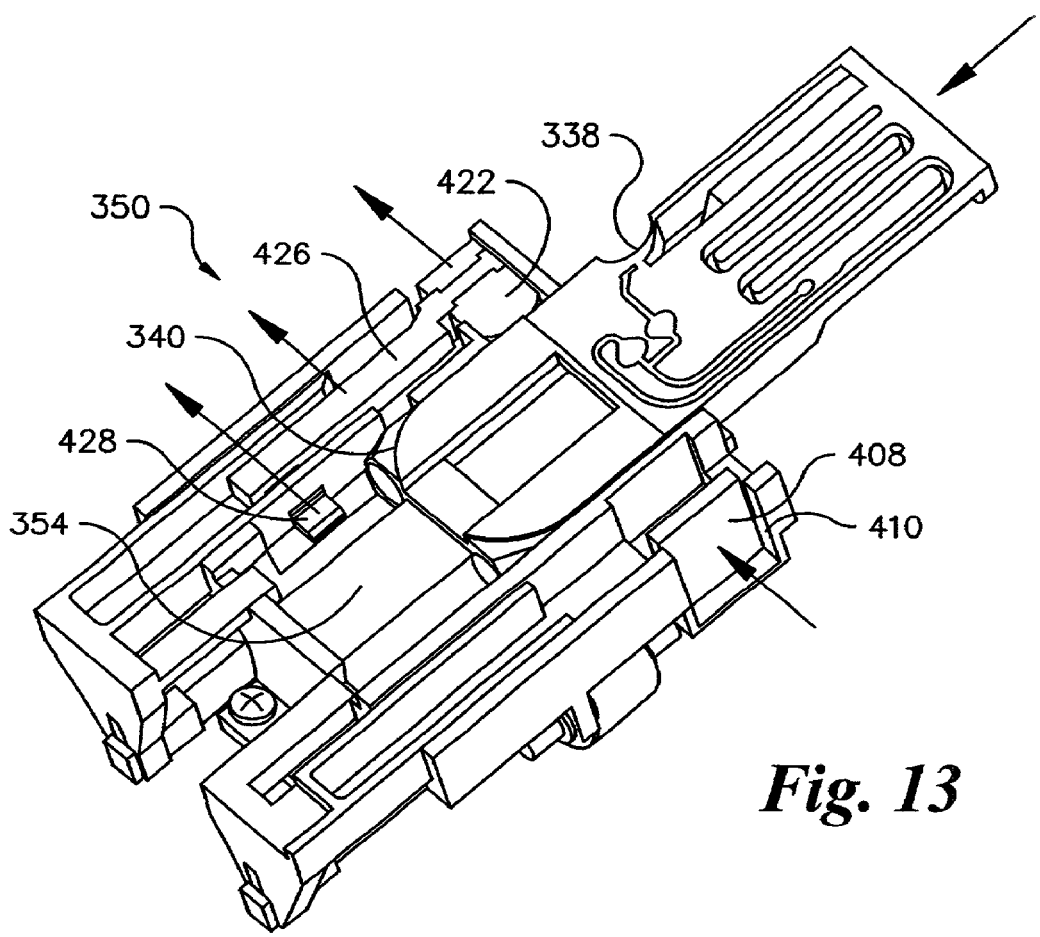

As best shown in FIGS. 9, 11, 12 and 13, the analysis station 302 further includes a moveable locking assembly which is employed for receiving and effectively locking a test cell 300 in place, when inserted in the proper manner as will hereinafter be described. The locking assembly includes an elongated detent slide member 404 which includes an elongated base portion 406 which extends laterally across the undersurface of the analysis station housing 350 as shown in FIG. 11. A first end of the base portion 406 includes an upwardly extending lug 408 which is received within a suitably sized opening 410 in the second wall 358 of the analysis station housing 350. A small compression spring 412 which preferably is made of steel, extends between the lug 408 and the third wall 360 of the analysis station housing 350 for the purpose of biasing or urging the lug 408 and, thus, the detent slide member 404 outwardly with respect to the analysis station housing 350. Thus, when the spring 412 is not compressed the detent slide member 404 is positioned with the lug 408 essentially coplanar with the second wall 358 of the analysis station housing 350 as shown in FIG. 12. The other end of the base portion 406 includes an irregularly shaped upwardly extending portion 414 which extends through a suitably sized slotted opening 416 in the analysis station housing 350. The upwardly extending portion 414 includes a generally flat member 418 which extends through a suitably sized opening 420 in the fifth wall 364 of the analysis station housing 350. The flat member 418 includes a generally curved forward edge 422 having a curvature which generally corresponds to the curvature of the cutout portion 338 of the test cell 300. The flat member 418 further includes an irregularly shaped slot 424 generally aligned with the open area between the fourth wall 362 and the fifth wall 364 of the analysis station housing 350. The slot 424 receives a first complimentary shaped end of an elongated arm blade 426. The arm blade 426 extends generally between the legs 370, 372 of the first elongated slide member 366 as shown in FIG. 12. The opposite end of the arm blade 426 is slidably connected, by a slot, to a negative pressure blade 428. The negative pressure blade 428, in turn, extends through a suitably sized opening 429 in the leg 372 of the first elongated slide member 366. In this manner, as the first elongated slide member 366 slides with respect to the analysis station housing 350, the negative pressure blade 328 moves longitudinally with the leg 372 of the first slide member and slides longitudinally along the arm blade 426. An elongated open area 430 is provided within the fifth wall 364 of the analysis station housing 350 to permit sliding longitudinal movement of the negative pressure blade 328. However, because the negative pressure blade 428 is connected to the leg 372 of the first elongated slide member 366 only by being captured within the opening 429, the negative pressure blade 428 is also capable of moving inwardly and outwardly with respect to the leg opening 429 upon movement of the arm blade 426. Thus, movement of the detent slide member 404 against the bias of the spring 412 (i.e., upon insertion of a test cell 300) results in the flat member 418 moving outwardly as shown in FIG. 13. Outward movement of the flat member 418 results in a similar outward movement of the arm blade 426 and a corresponding outward movement of the negative pressure blade 428 for purposes which will hereinafter become apparent. Similarly, movement of the detent slide member 404 in the opposite direction because of decompression the spring 412 results in inward movement of the flat member 418 and corresponding inward movement of the arm blade 426 and movement of the negative pressure blade 428 into the opening the opening 429.

A cover member 432 is positioned over the top surface of the analysis station housing 350. The cover member 432 is generally flat and includes three generally rectangularly shaped openings 434, 436, 438 each of which is adapted to receive a generally rectangularly shaped proximity switch 440. The proximity switches 440 are engaged by upwardly extending members on the first and second elongated slide members 366, 376 and on the detent slide member 404 for the purpose of providing a positive indication to the microprocessor 500 with respect to the location of the first and second elongated slide members 366, 376 and the detent slide member 404 for control purposes. The microprocessor 500 receives the information from the proximity switches 440 by way of electrical contacts and suitable wiring (not shown) to assist the microprocessor 500 in controlling the performance of the diagnostic testing as will hereinafter be described in greater detail.

The central portion of the cover member 432 includes a larger generally rectangularly shaped opening 442 extending therethrough. The opening 442 is located so as to be generally aligned with the central wall 354 when the cover member 432 is installed on the upper surface of the analysis station housing 350. The opening 442 is provided for receiving an electrical contact assembly 444 to facilitate electrical contact between the contacts 332A, 332B and 332C on the electrode/contact pad assembly 328 of a test cell 300 and the microprocessor 500 within the instrument 10. The contact assembly 444 is comprised of a support member 446 which receives and supports a printed circuit board 448 and an electrical contact board 450. The under surface of the electrical contact board 450 includes a plurality of electrical contacts (not shown) which are arranged in the same manner as the contacts 332A, 332B, 332C on the electrode/contact pad assembly 328 of the test cell 300. The printed circuit board 448 provides electrical paths on the upper surface thereof which are electrically connected to the contacts on the under surface of the contact board 450. The support member 446 in turn is supported on the distal end of an elongated spring member 452 which is secured to the analysis station cover member 432. As shown in FIG. 9, the spring member 452 is bent in such a way that it urges the support member 446, printed circuit board 448 and contact board 450 downwardly through the opening 442 of the cover member 432 and into the area of the analysis station housing 350 above the central wall 354. In this manner, the contact assembly 444 can move upwardly against the bias of the spring member 452 as needed for receiving a test cell 300. An analysis station printed circuit board 454 further covers the central portion of the cover member 432 as shown in FIG. 10.

Set forth below is a description of the manner in which the test cell 300 is employed in conjunction with the analysis station 302 for performing a diagnostic test. The test cell 300 includes a barcode 101 as well as the other safety features described above and below to make sure that the test cell 300 which is inserted into the instrument 10 is correct for the diagnostic test to be performed. In addition, as best shown in FIGS. 6 and 13, the griping end 308 of the test cell housing 304 includes a downwardly extending lip member which is too large to fit into the test cell receiving opening (i.e., slot 34 of the housing 12) of the analysis station housing 350. In this manner, it is not possible to insert the griping end 308 of the test cell 300 into the analysis station 302. Likewise, the shape of the opening of the test cell housing 350 is such that the test cell 302 may only be inserted as shown FIG. 14, with the cylindrical portions 311 and 313 extending downwardly. Except as otherwise stated, the analysis station 302 is preferably made of Acetal or some other such polymeric material.

As previously mentioned, the calibration capsule 314 is initially installed within the first bore 310 of the test cell housing 304 and need not be removed for the performance of a diagnostic test. On the other hand, the specimen capsule 316 is first used to obtain a specimen of the blood or other bodily fluid of the patient to be tested. To obtain the specimen the squeezable portion 318 of the specimen capsule 316 is squeezed and then placed with the fluid proximate the opposite open end of the specimen capsule 316. Thereafter, the squeezable portion 318 is released to effectively suck the specimen into the specimen capsule 316 in the manner of a pipet. Once the specimen to be tested has been sucked into the specimen capsule 316, the specimen capsule 316 is placed within the second bore 312 of the test cell housing 304 as shown. The bore 312 controls the insertion of the capsule 316.

After taking the appropriate barcode reading, the test cell 300 with the specimen to be tested within the specimen capsule 316 is pushed into the opening in the analysis station housing 350. As previously stated, the analysis station 302 is located within the instrument 10 so that the opening of the analysis station 302 is in the same position as the slot 34 on the side of the housing 12 of the instrument 10. As previously stated, the test cell 300 may only be installed within the opening of the analysis station 302 with a single orientation, that is, with the insertion end facing inwardly and with the cylindrical portions 311 and 313 facing downwardly as shown in FIG. 13.

Figure 14:
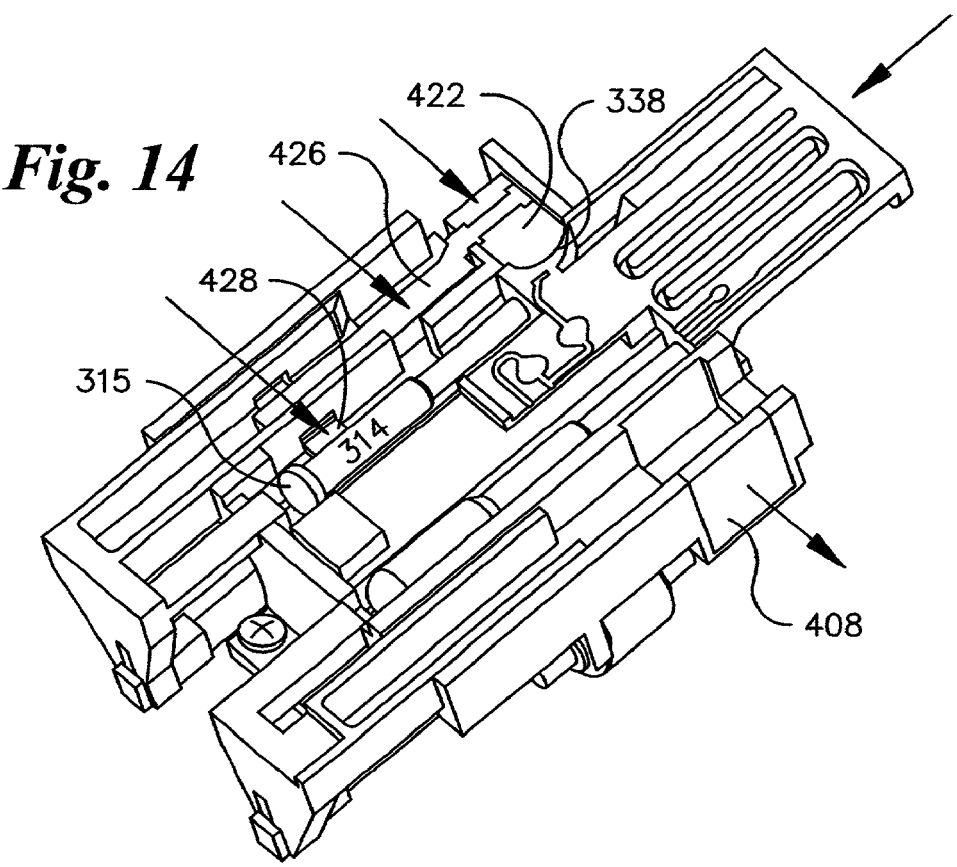

FIG. 13 shows a test cell 300 partially installed within the analysis station housing 350 with cover member 432 removed for clarity. As the test cell 300 is pushed inwardly, the curved or bevel portion 340 on the upper surface of the test cell housing 304 engages the curved portion 422 on the detent slide member 404 causing the detent slide member to move against the bias of the spring 412 toward the left when viewing FIG. 13 as shown by the arrows. As previously discussed, movement of the detent slide member 404 also moves the arm blade 426 and the negative pressure blade 428 outwardly as illustrated by the arrows in FIG. 13. At this stage of the installation of the test cell 300, the cylindrical portions 311 and 313 engage the area between the central wall 354 and the fifth wall 364 on one side and the third wall 360 on the other side. The electrode/contact pad assembly 328 engages and moves along the upper surface 356 of the central wall 354. Correspondingly, the upper surface of the insertion end 306 of the test cell housing 304 engages the undersurface of the cover member 432. The clearances between the various components of the analysis station housing 350 and the test cell housing 304 are sufficient to permit relatively free movement therebetween. FIG. 14 illustrates the test cell 300 as it appears when completely installed within the opening of the analysis station housing 350. For a better understanding of the relationship between these components, a portion of the test cell housing 304 has been cut away. When the test cell 300 is completely installed as shown, the curved portion 422 of the detent slide member 404 engages the arcuate cut out portion 338 of the test cell housing 304. This permits the detent slide member 404 to move toward the right as shown by the arrows when viewing FIG. 14 under the bias of the spring 412, so that the lug 408 is again generally parallel to the second wall 358 of the analysis station housing 350. The arm blade 426 correspondingly moves to the right as illustrated by the arrows, which in turn move the negative pressure blade 428 to the right. The negative pressure blade 428 extends into the elongated slot 344 on the lateral side of the test cell housing 304 and generally into engagement with the calibration capsule 314. Note that the distal end of the calibration capsule 314 includes an annular cap member 315 on its rear end with a diameter which is slightly greater than the diameter of the remainder of the calibration capsule 314. The negative pressure blade 428 engages the cap member 315 in a manner which will hereinafter be described to provide outward movement of the calibration capsule 314. The sloped insert 342 on the forward end of the test cell housing 304 causes the contact assembly 444 to move upwardly against the bias of the spring member 452 as the test cell housing 304 is being pushed into the analysis station housing 350. Once the contact assembly 444 has moved beyond the sloped insert 342 of the test cell housing 304, the bias of the spring member 452 moves the contact assembly 444 downwardly to positively engage the contacts 332A, 332B, 332C of the electrode/contact pad assembly 328 to provide positive electrical contact between the test cell 300 and the microprocessor 500. Once the test cell 300 is fully inserted within the analysis station housing 350, the sliding movement of the detent slide member 404 locks the test cell 300 in place and concurrently activates the corresponding proximity switch 440 to signal the microprocessor 500 that a diagnostic test is ready to proceed.

Figure 15:
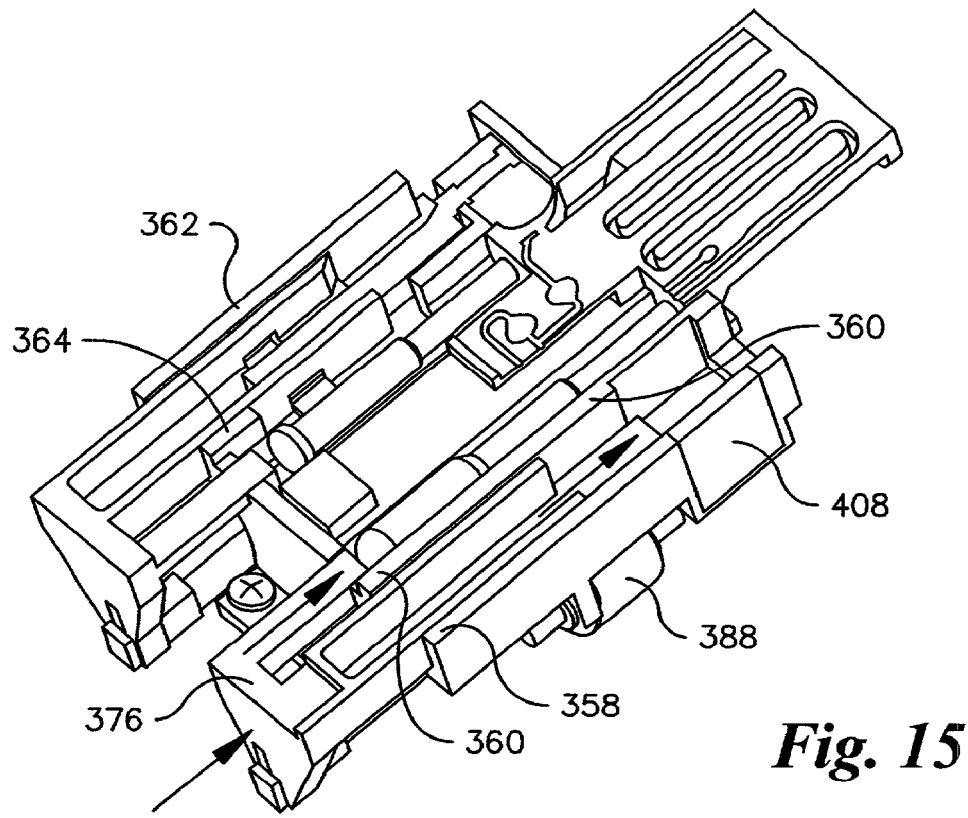

The remaining steps in performing the diagnostic analysis are described below with respect to FIGS. 15–21. As shown in FIG. 15, in the first step linear actuator 388 moves its lead screw 394 inwardly a short distance (from being extended 0.65 inches to being extended 0.575 inches) so that the forward web portion of the second slide member 376 is located between the lug 408 of the detent slide member 404 and the third wall 360 of the analysis station housing 350. The forward web portion of the second slide member 376 thereby effectively prevents the detent slide member 404 from sliding toward the left, thereby effectively locking the test cell 300 in place within the analysis station housing 350. At this stage, neither of the elongated slide members 366, 376 have caused any movement of the fluids within the calibration capsule 314 or the specimen capsule 316.

Figure 16:
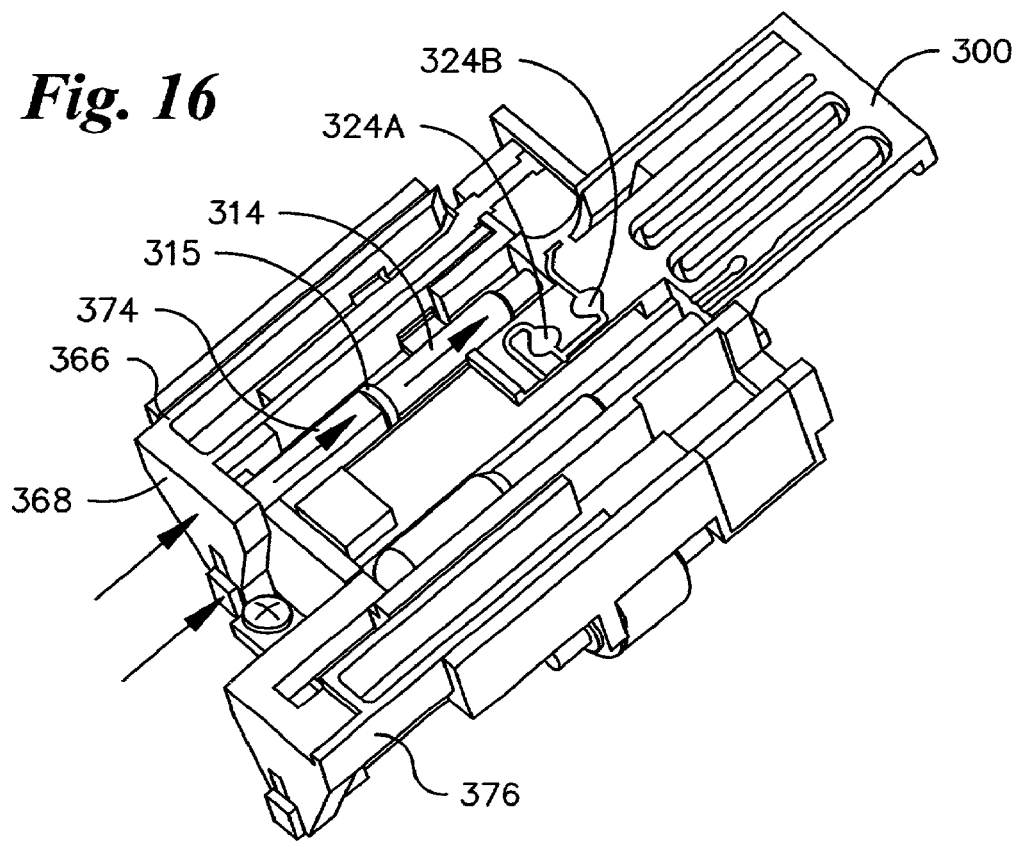

FIG. 16 illustrates the next step in the performance of a diagnostic test. As shown in FIG. 16 linear actuator 386 moves its lead screw 392 inwardly thereby causing the first slide member 366 to translate inwardly as shown. Leg 374 of the first slide member 366 engages the cap member 315 of the calibration capsule 314 and effectively pushes the calibration capsule 314 further into the bore 310 of the test cell housing 304 as illustrated by the arrows on FIG. 16. The inward movement of the calibration capsule 314 pumps the calibration fluid out of the calibration capsule 314 by displacement, forcing the calibration fluid to flow through the corresponding tube 320 and fluid passageway and into the electrode chambers 324A, 324B. Any excess calibration fluid which overflows the electrode chambers 324A, 324B flows through a fluid passageway and into the serpentine passageway 326. The first slide member 366 moves a distance of 0.55 inch so that it is completely in the analysis station housing 350 with its vertical base 368 engaging the analysis station housing 350 as shown in FIG. 16. At this point, calibration of the electrodes 330A, 330B within the electrode chambers 324A, 324B proceeds for a predetermined controlled time. During the calibration period the calibration fluid is exposed to the membranes and ions are absorbed on the membranes. The number of ions absorbed depends on the concentration and chemistry of the calibration fluid which is specifically selected for each diagnostic test. The voltage potential across the electrodes 330A, 330B is measured continuously during calibration. The measured potential is proportional to the logarithm of the concentration of the calibration fluid. The measurement continues until a stable potential is attained. Once calibration of the electrodes 330A, 330B within the electrode chambers 324A, 324B has been completed, the blood or other fluid to be diagnosed is inserted into one of the electrode chambers 324A.

Figure 19:
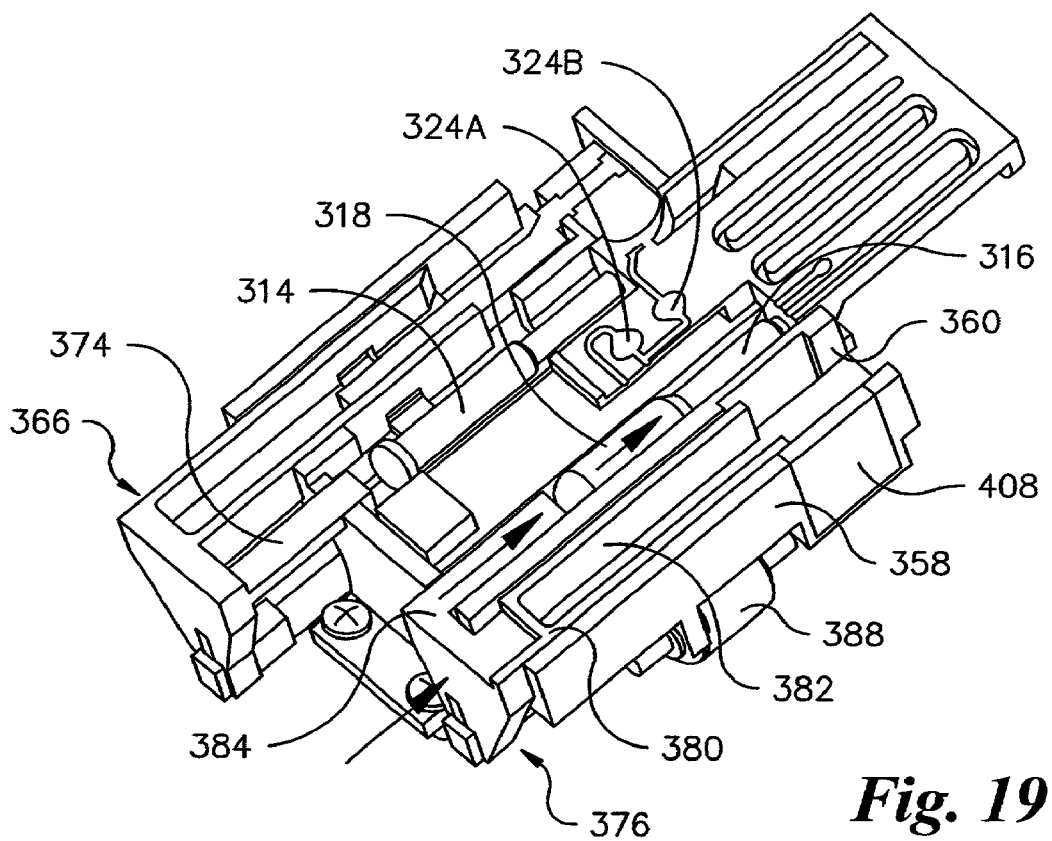

FIG. 19 illustrates the next step in the process. As shown in FIG. 19, the linear actuator 388 retracts its lead screw 394 thereby moving the second slide member 376 into the analysis station housing 350 as illustrated. The leg 384 of the second slide member 376 engages the squeezable portion 318 of the specimen capsule 316 to push the specimen capsule 316 further into the bore 312, thereby causing the blood or other fluid within the specimen capsule 316 to be displaced and pumped through the corresponding tube 322 and fluid passageways and into the electrode chamber 324A. Air in front of the blood or other specimen fluid pushes the calibration fluid out of electrode chamber 324A. The calibration fluid which was in electrode chamber 324A and any excess blood or other fluid which overflows electrode chamber 324A flows through a fluid passageway and into the serpentine passageway 326. The blood or other fluid is prevented from flowing into electrode chamber 324B because of the presence of the calibration fluid in electrode chamber 324B and the lack of egress for the fluid. As shown in FIG. 19, the second slide member 376 slides completely inwardly a distance of 0.575 inch with the vertical base 378 engaging the analysis station housing 350. At this point, a salt bridge is established between the two electrode chambers 324A and 324B and the analysis of the blood or other fluid proceeds under the control of the microprocessor 500. During the test period the blood or other fluid being tested is exposed to the membrane and ions are selectively absorbed on the membrane. The potential across the electrodes 330A, 330B is measured until a stable potential is attained as a result of equilibration. The stabilized potential is compared to the stabilized potential obtained during calibration and the difference is used, with stored information to calculate the concentration of the analyte in the blood or other fluid.

Figure 17:
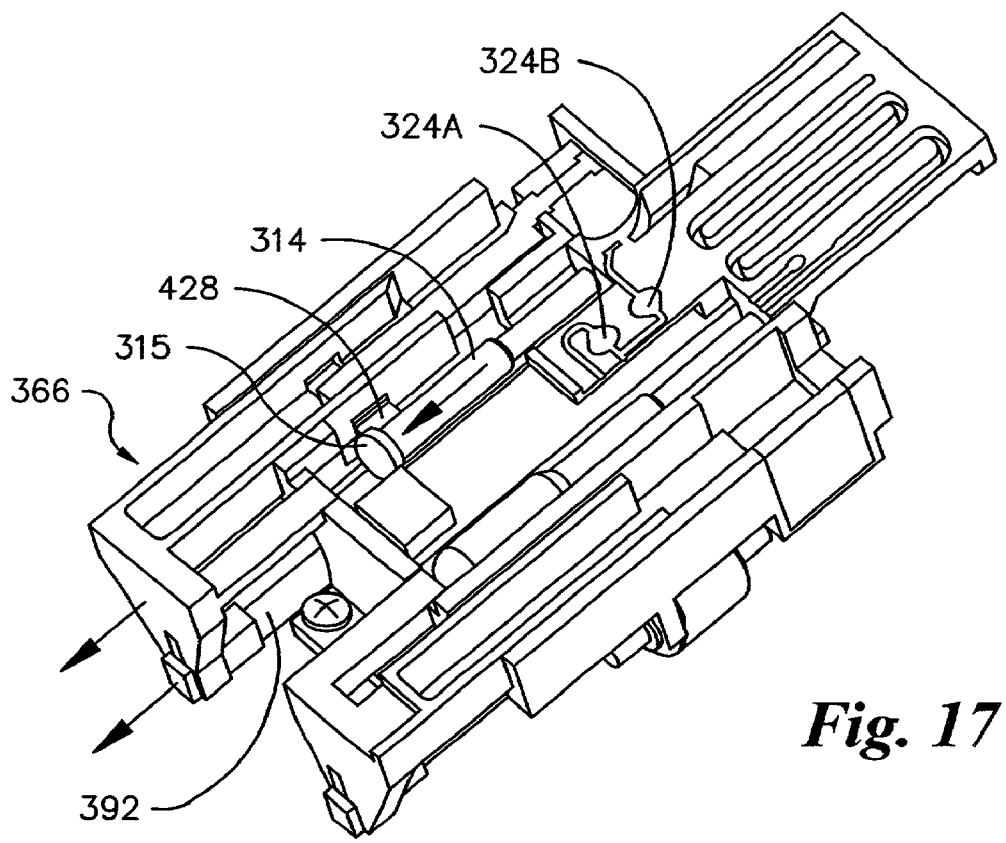
Figure 18:
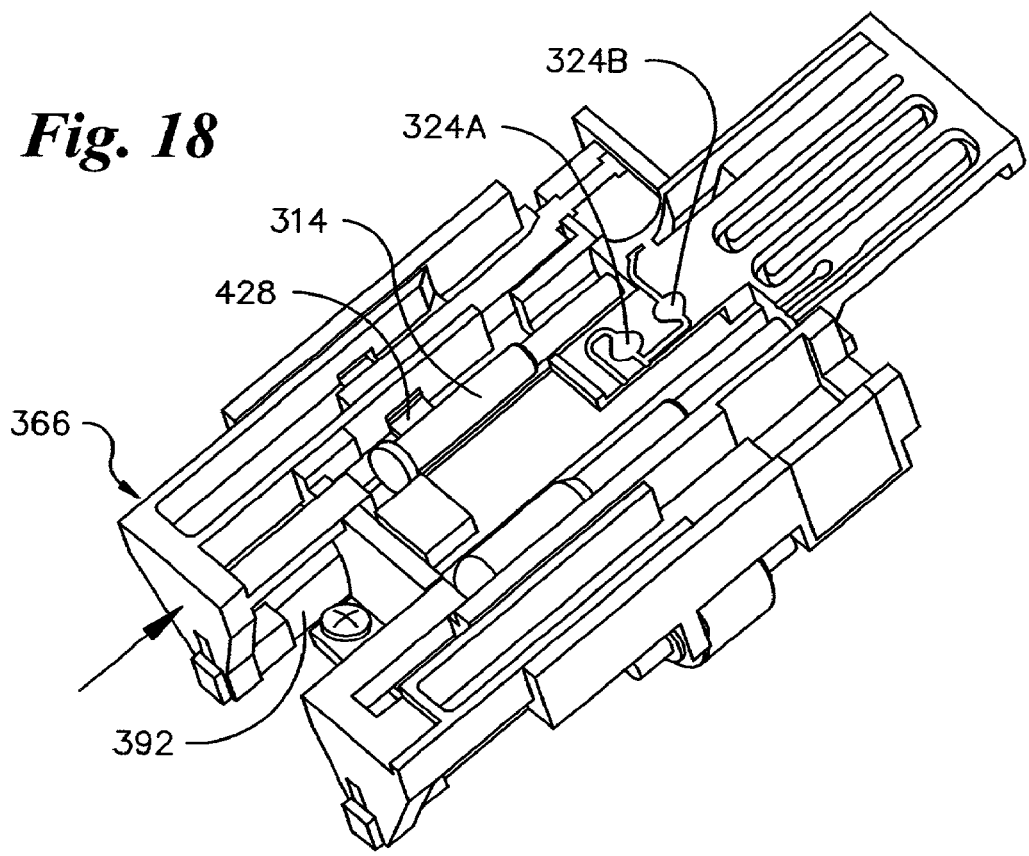
Figure 20:
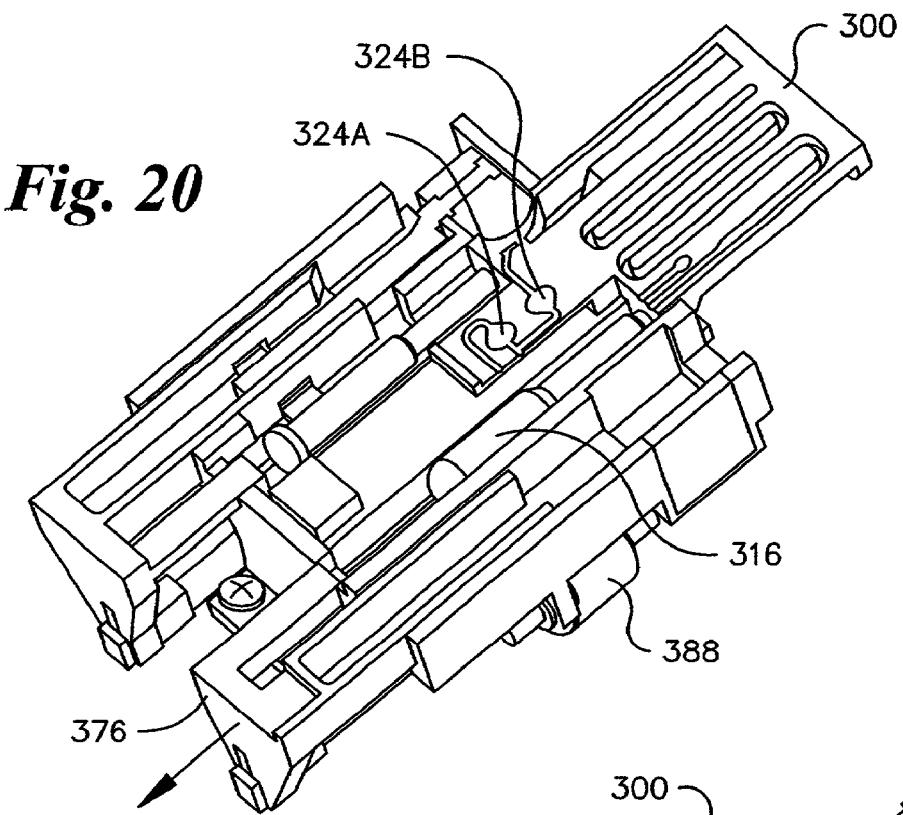
Figure 21:
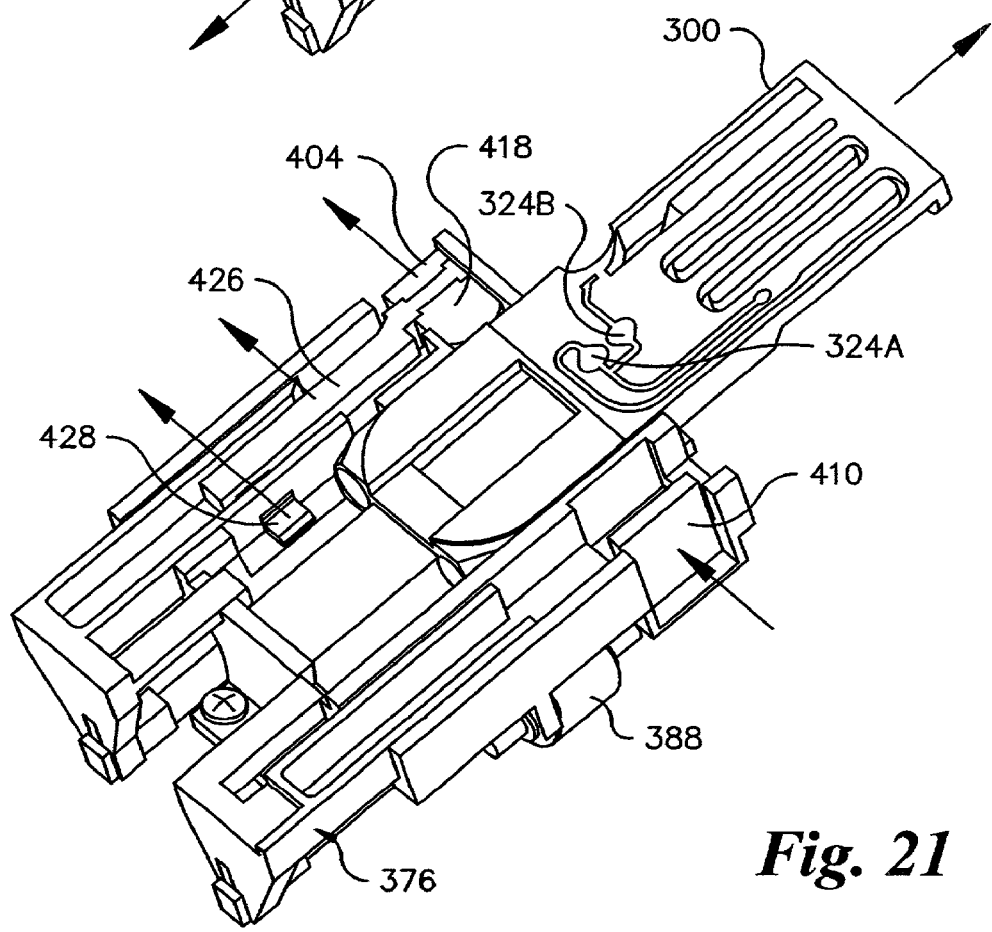

Once the analysis of the blood or other fluid has been completed, the linear actuator 386 moves its lead screw 392 outwardly thereby causing the first slide member 366 to translate outwardly as shown in FIG. 17. The outward translation of the first slide member 366 causes corresponding movement of the negative pressure blade 428 along the arm blade 426. The negative pressure blade 428 extends through the test cell housing slot and engages the cap member 315 of the calibration capsule 314 to thereby pull the calibration capsule 314 outwardly with respect to the corresponding tube 320 as shown in FIG. 18. The outward movement of the calibration capsule 314 creates a suction or reduced pressure which draws calibration fluid from the electrode chamber 324B and blood from electrode chamber 324A through the fluid passageways and the corresponding tube 320 and back into the calibration capsule 314. As shown in FIG. 17, the first slide member 366 moves outwardly so that the first slide member 366 again resumes its initial position i.e., 0.55 inch out of the analysis station housing 350 as shown in FIG. 18. The linear actuator 388 also moves its lead screw 394 outwardly to thereby move the second slide 376 outwardly as shown in FIG. 20 to its original position (FIG. 12). The movement of the linear actuators 386, 388 may occur simultaneously, if desired, to simultaneously retract both slide members 366, 376. Moving the second slide member 376 outwardly in this manner effectively releases the detent slide 404 so that it may now be slide to the left when viewing the figures. Releasing the detent slide 404 permits the test cell 300 to be removed from the analysis station housing 350 by merely grasping the gripping end 308 and pulling outwardly as indicated by the arrow on FIG. 21. The pulling outwardly of the test cell 300 effectively overcomes the bias of the detent slide member spring 412 to move the flat member 418, arm blade 426 and negative pressure blade 428 toward the left as shown by the arrows to effectively release the test cell 300. Once the test cell has been removed from the analysis station housing 350, it should be disposed of in a safe manner because it is not reusable. Of course, all of the blood or other fluid being tested remains captured within the calibration capsule 314, specimen capsule 316, electrode chambers 324A, 324B and, if necessary, in the overflow serpentine passageway 326 to prevent any possible contamination problems from arising. The analysis station 302 and in particular, the first and second slide members 366, 376 are now in their respective initial positions as shown in FIG. 40 and are ready for receiving another test cell 300. Subsequent testing and analysis may be conducted in the same manner (using a new test cell 300) as described above.

As previously discussed, the instrument 10 has the capability of performing a variety of different real time medical diagnostic tests with each test using a single disposable test cell 300 which has been specifically designated for the particular diagnostic test. Each test cell 300 contains all of the correct calibration fluid, electrodes, electrolyte, etc. for a particular medical diagnostic test. A bar coded label 101 on each test cell 300, as well as the color of the test cell identifies the particular test that the test cell 300 is to perform, as well as the relevant control parameters for the particular test. In this manner, the instrument 10 is adapted for automatic customization, through software, for the performance of the various medical diagnostic tests.

The software employed in the instrument 10 includes a full featured operating system, in the present embodiment WIND River VxWorks, which supports network connectivity, C++ applications and advanced real time software development tools. The software provides input/output and power management functions as described including a simple, menu-based operator interface; parameter driven functions to control and analyze the diagnostic tests; and an internal non-volatile filing system to store test protocols and test results. Stored test results can be recalled and displayed, printed out and/or read out to another device or network. The software allows for the addition of protocols for new diagnostic tests through simple file downloading. The operating software has been created using ObjectTime, a very high level, portable real time graphical software design system that generates C++ code from hierarchical state charts. The state charts define the behavior of a finite state machine that responds to external signals or messages received from other processes by modifying the internal states. ObjectTime thus defines a system as a collection asynchronous processes that communicate with each other by exchanging messages. FIGS. 22–27 are state chart diagrams of the principal software process of a preferred embodiment of the instrument 10 define in terms of state and state transition paths.

Figure 22:
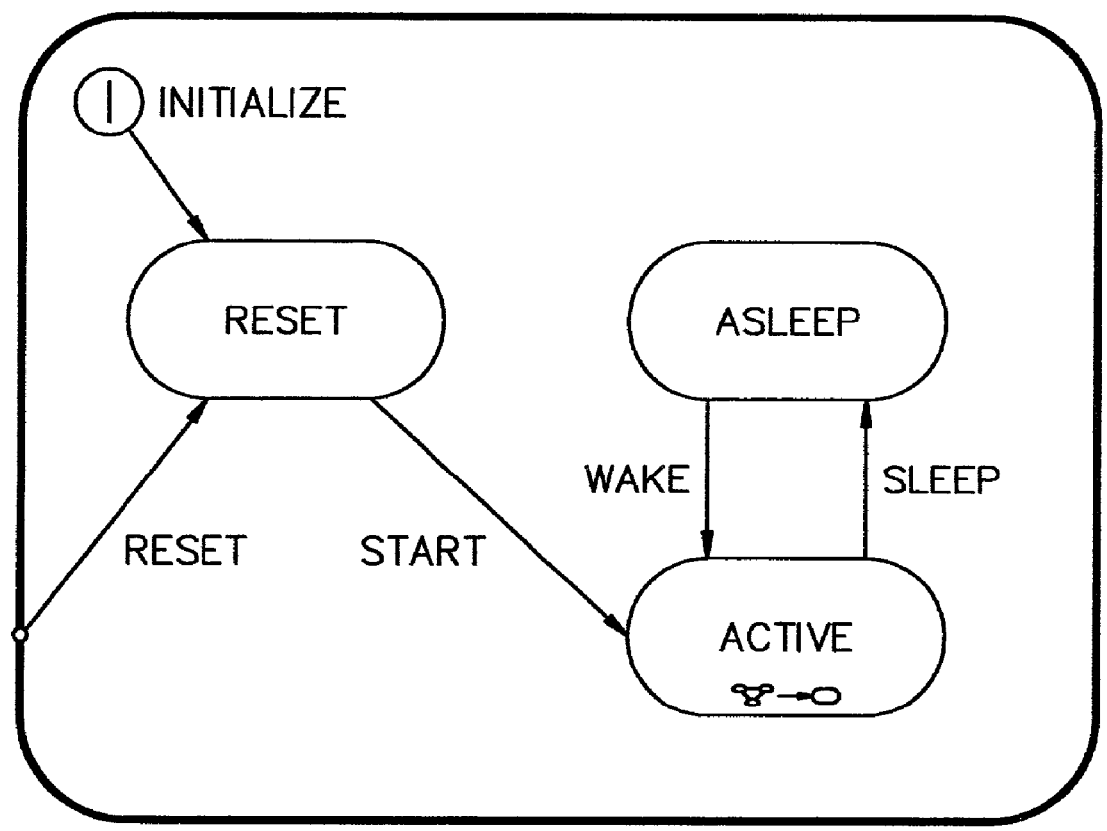
FIGS. 22–27 are a series of nested hierachial state chart diagrams which illustrate the functioning of the software of a preferred embodiment of the present invention in terms of processes and communication paths.
Figure 25:
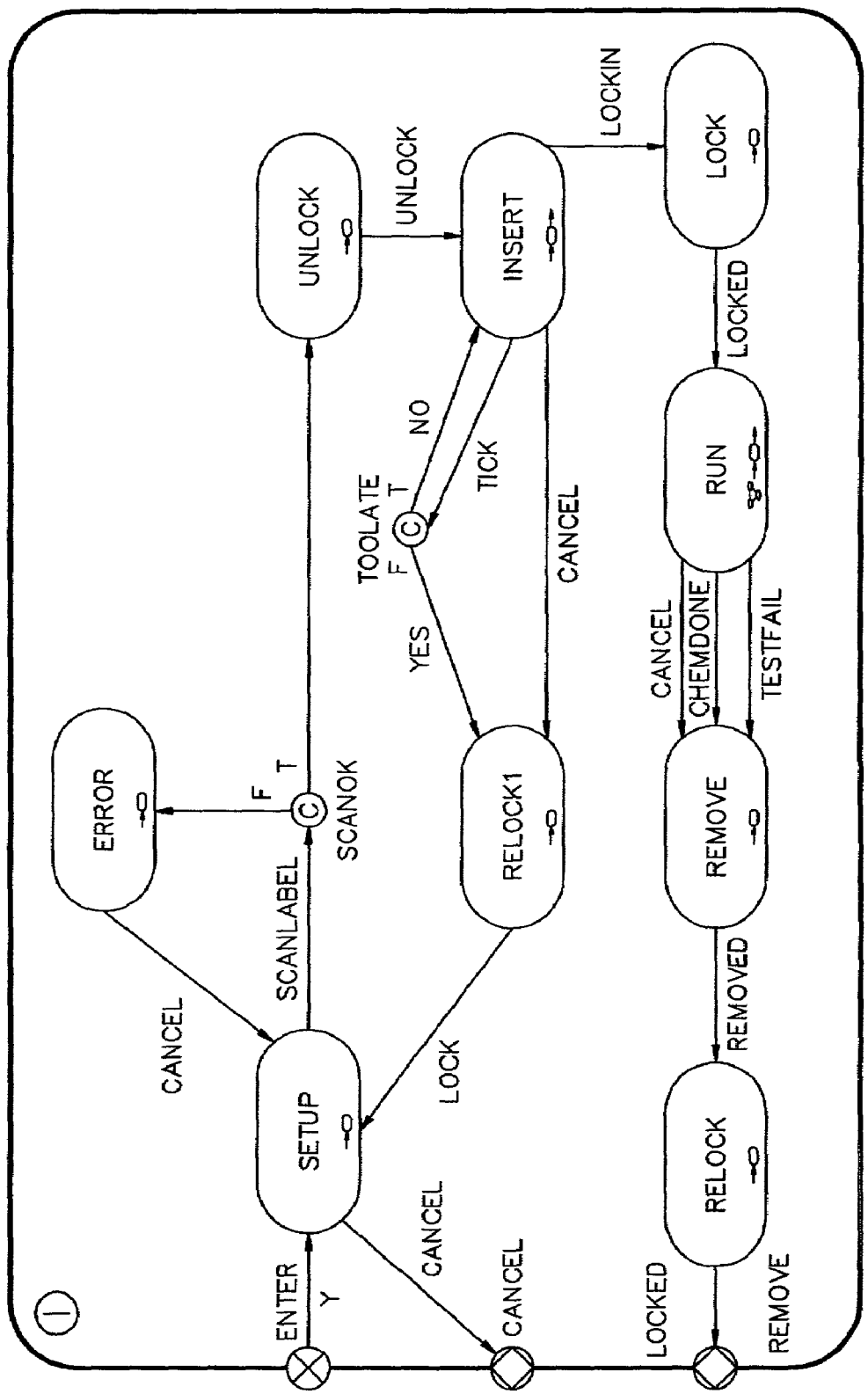
Figure 26:
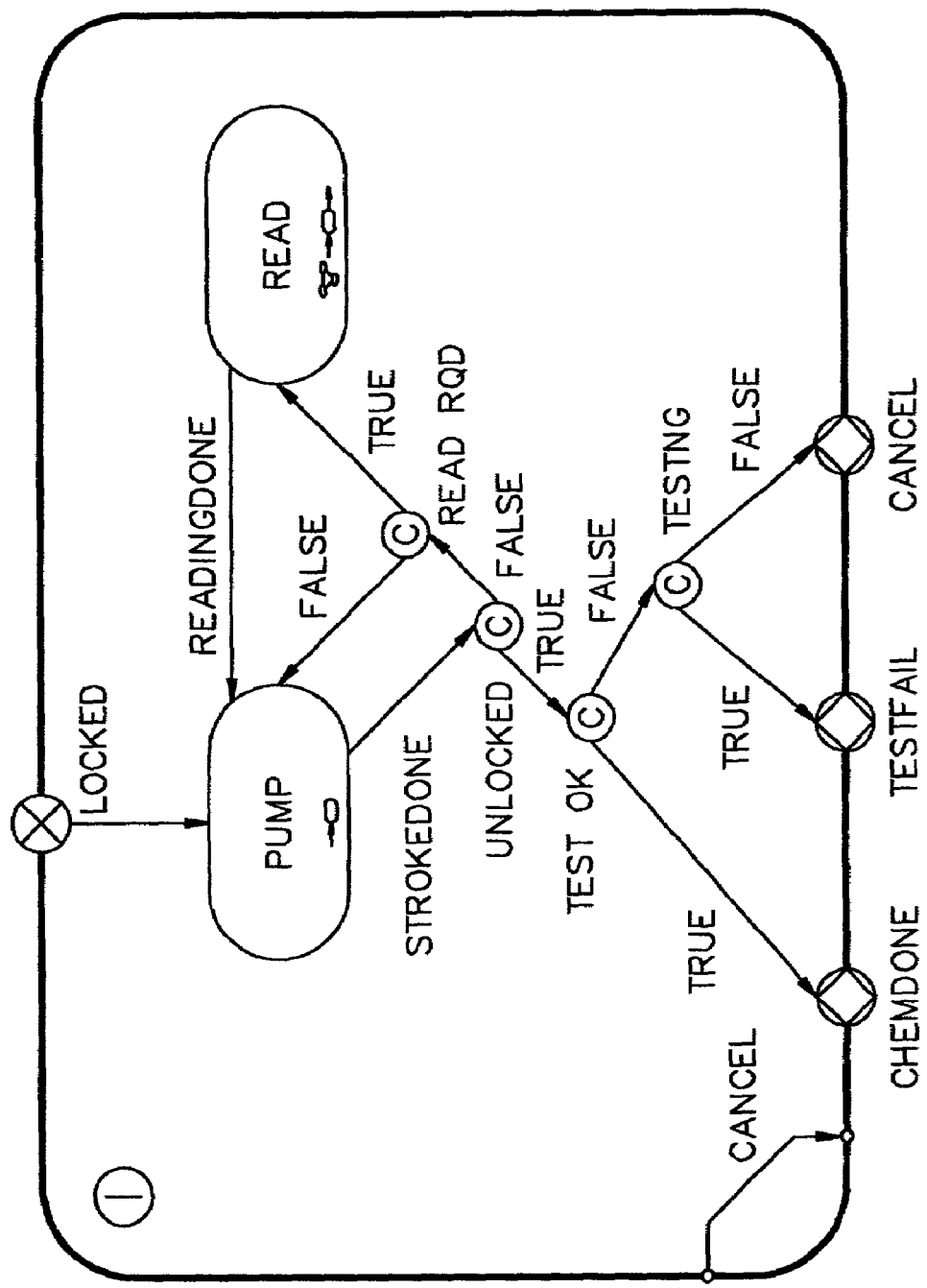
Figure 27:
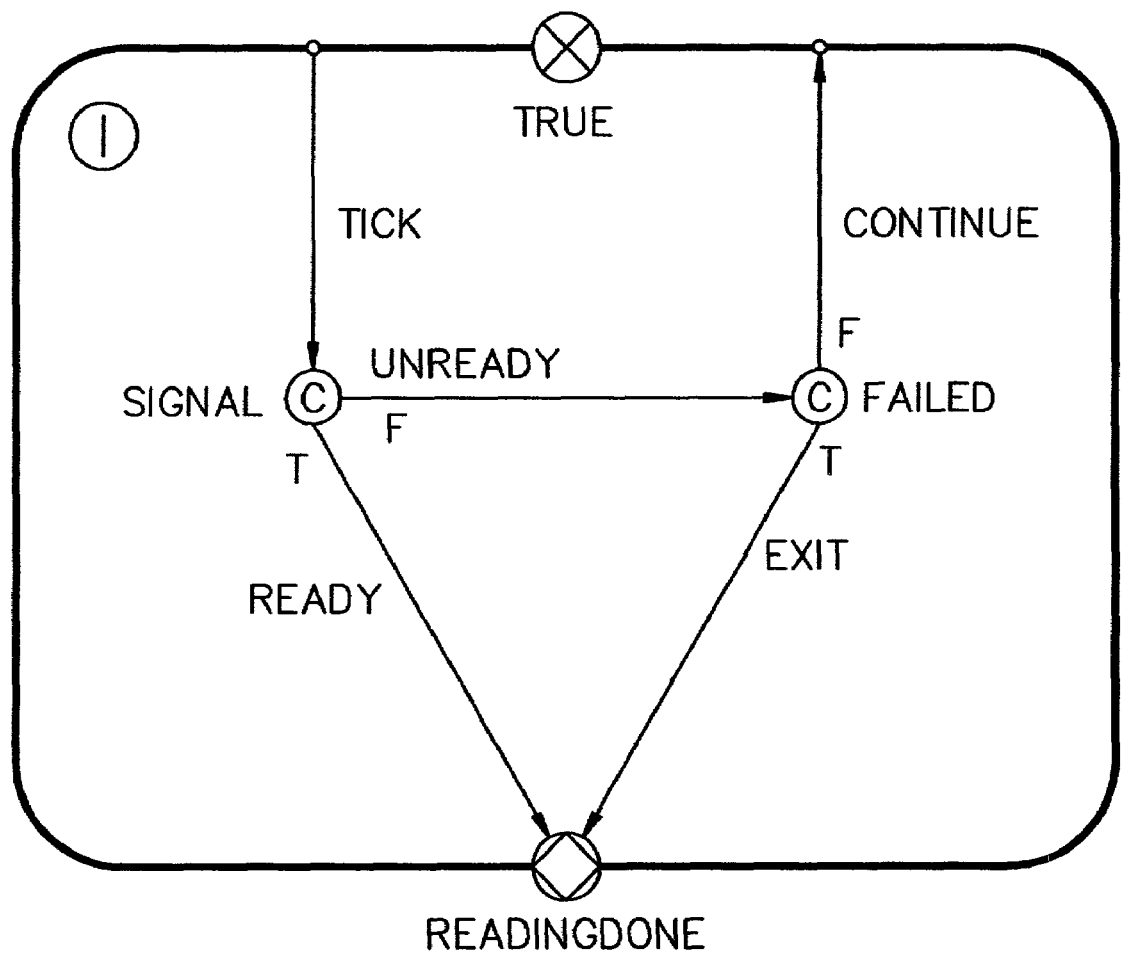

The state chart diagrams of FIGS. 22–27 describe a single nested hierarchy of behavioral stares that illustrate the operation of the preferred embodiment of the instrument 10. In FIGS. 22–27, the more generic behaviors appear at the outer levels and the more specific behaviors appear at the inner levels. The outermost level called Top is shown in FIG. 22 and the innermost level, called read IN run IN DoATest IN Run IN Active IN Top is shown in FIG. 27. Each of the diagrams illustrated by FIGS. 22–27 appears as a single state on the preceding, next outermost diagram. Thus, the boundary of each diagram is the boundary of a state. Each large oval-shaped area inside a diagram represents another, more interior state. An arrow or sequence of arrows shows how the software process functions to move from state to state. The process leaves a state only in response to a specific event and never of its own accord. Once the process of leaving a state is launched, the process does not stop until it reaches the next state. Some events are generated by timers attached to the process, other events are the result of operator actions and still other events result from signals obtained from the analysis unit 302, stepper motor driver 532 or other devices. Several other processes detect the events while providing services such as reading barcodes and parsing inputs from keys.

The small circles on the diagram of FIGS. 22–27 represent the decision points where the process chooses which of two arrows to follow next by evaluating a logical test. The tests never involve waiting for another event, each event makes the process follow a complete path from one state to another state or back to the same state.

Paths that connect to the edge of a chart have special properties. The presence of a circled symbol indicates that the path continues in the next higher level of the hierarchy; that is, control enters or leaves the chart from the circled symbols. If there are no symbols, the arrow represents an exit from, or a return to, a state in the current chart, whichever state the process was in when a triggering event occurred. Thus, an arrow that starts and ends on the boundary functions like an interrupt service routine or exception handler in that it can start in any state on the chart and thereafter return the process to the same state.

In the diagrams, program code is executed "in the arrows". An arrow may have a C++ procedure attached to it and every decision point has a procedure that evaluates a test. Additional procedures can be executed whenever a particular state is entered, or exited, regardless of the path. Thus, the ObjectTime diagram defines the sequence of actions, which are performed by ordinary C++ and C subroutines. Many of the subroutines reside in external libraries and access facilities, such as input/output signal processing, test cell label parsing, time and date, memory files, etc.

FIG. 22 illustrates the outermost level called Top. FIG. 22 illustrates re-initialization of the process on power-up or hardware reset and then the process alternating between an active state and an inactive state in which the hardware is "put to sleep" to conserve battery power. The sleep signal comes from a counter, driven by the system clock, that is reset each time the process enters a new state. Wake signals come from the operator depressing a key on the front panel 17.

Figure 23:
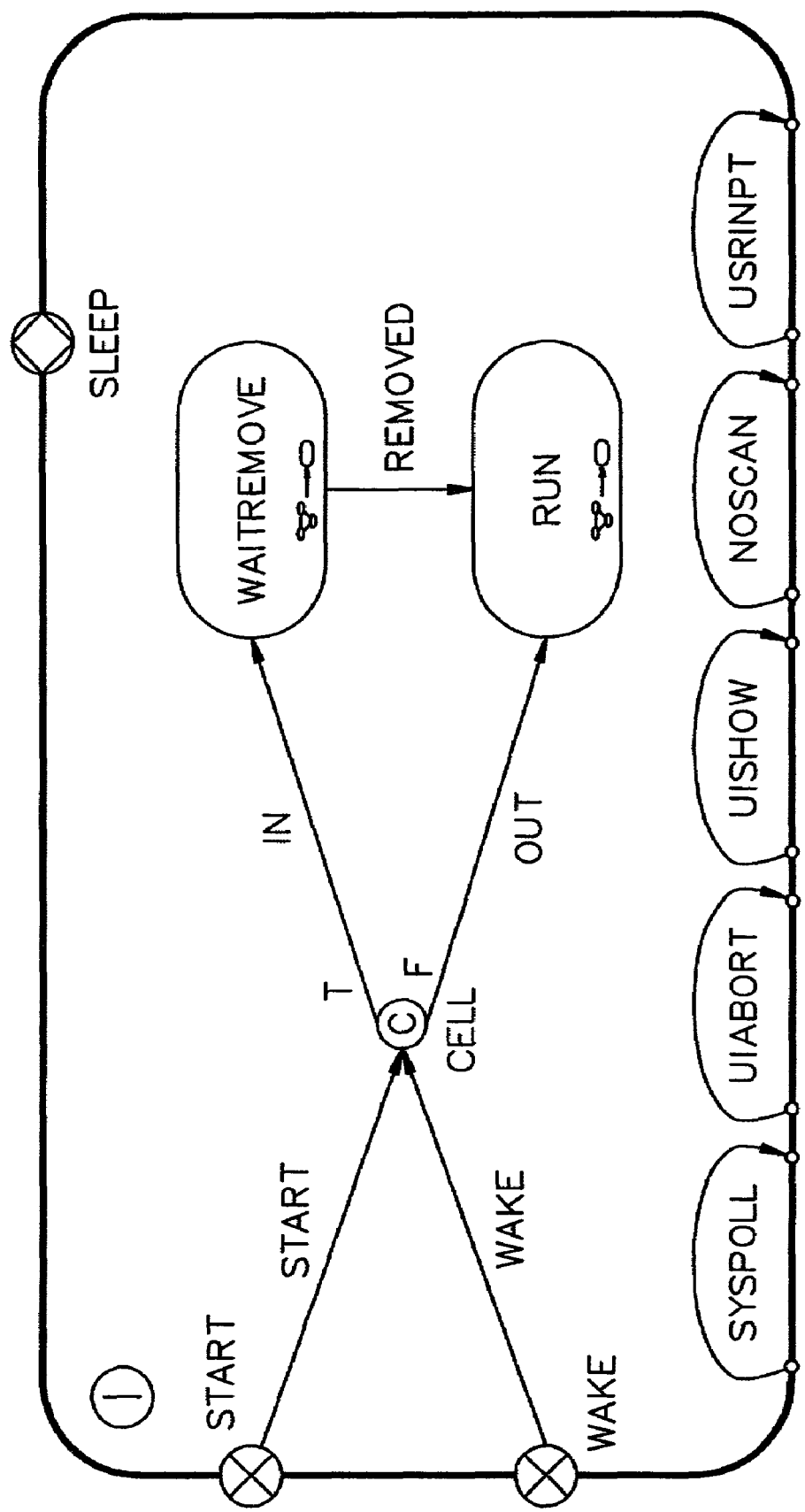

FIG. 23 illustrates the next innermost diagram Active IN Top. As illustrated, the process first checks to see whether a test cell 300 has been left in the analysis station 302 and, if so, alerts the operator and waits for the test cell 300 to be removed. When the analysis station 302 is clear of test cells 300, the process enters the normal running state. The "interrupt handlers" along the lower edge of the diagram perform service functions. For example, "SYSPOLL" functions once per second to refresh the date and time shown on the display 20. The other interrupt handlers relate primarily to the abortion of a diagnostic test under certain circumstances described above and below and are ignored when the process is in a working state.

Figure 24:
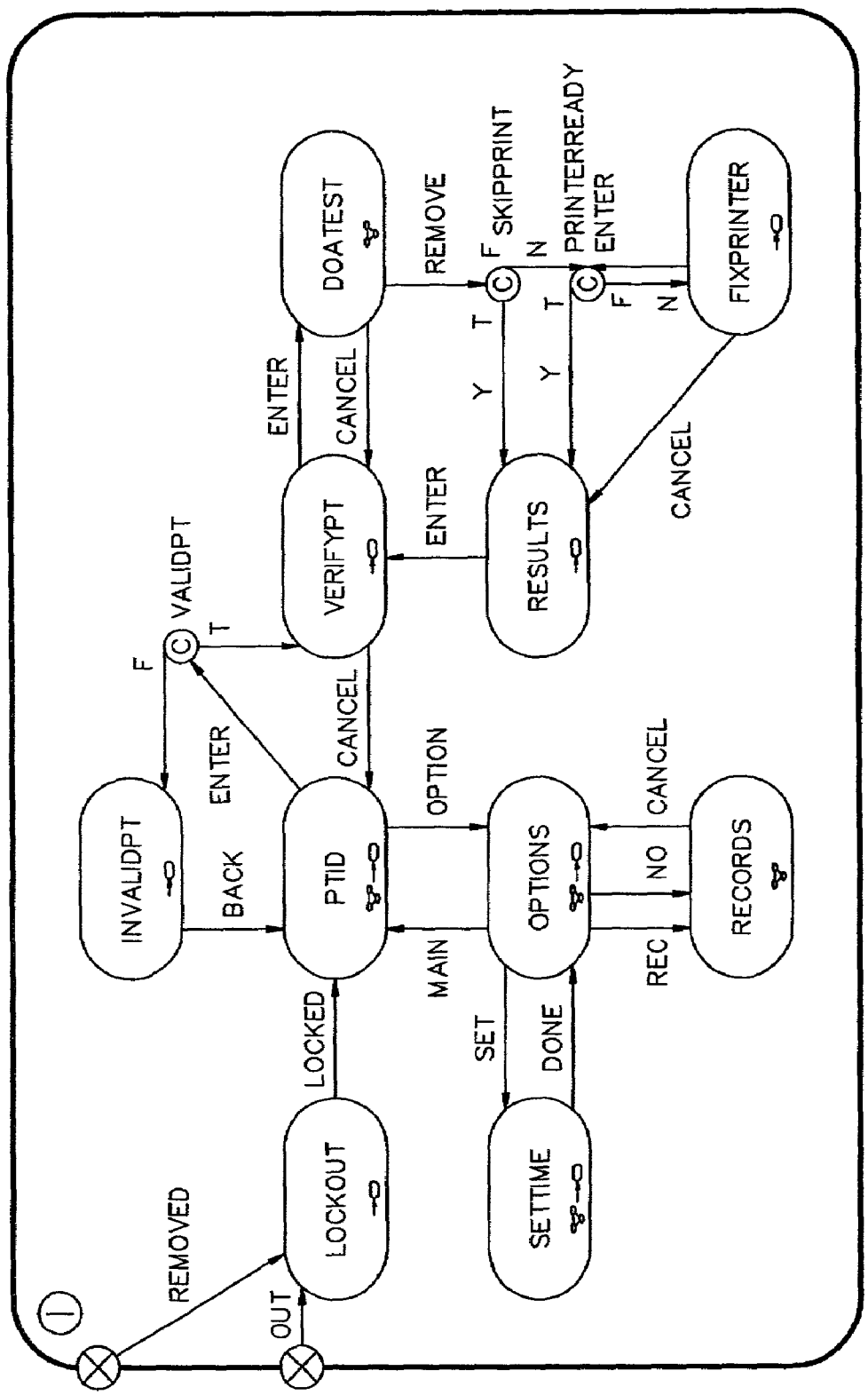

FIG. 24 illustrates the next innermost level called Run IN Active IN Top. FIG. 24 illustrates the processes of locking the analysis station 302, waiting for the operator to enter a patient ID or other requested information and waiting for the operator to verify that the patient identification information displayed on the screen is correct. When valid patient identification information has been entered and verified then the process is ready to perform the diagnostic test.

FIG. 25 shows the next innermost level called DoATest IN Run IN Active IN Top. In the diagram of FIG. 25, the process waits for the operator to scan a valid test cell barcode 101 and then insert the test cell 300 into the analysis station 302 within a predetermined time period. The process then locks the test cell 300 within the analysis station 302 as described above and the diagnostic test begins in the manner described above. The analysis station 302 is unlocked to release the test cell 300 when the diagnostic test ends and the operator is requested to remove the used test cell 300 and, once removed, the analysis station is again locked to prevent the insertion of a test cell 300 without new patient identification information being entered and verified (FIG. 24).

FIG. 26 shows the next innermost level called run In DoATest IN Run IN Active IN Top. In the diagram of FIG. 26, the process is stepping through a list of coded commands that specify the various steps involved in moving the calibration fluid and blood or other bodily fluid into and out of the electrode chambers and controlling the reading of the voltages involved in the performance of the diagnostic test. If a recording signal is called for, a read state is entered, which results in the posting of a test failure condition or a good test signal. When in a pump state, the process waits until the pumping is completed. The decision point "unlocked" identifies the end of the pumping/testing schedule. The interrupt handler "cancel" posts an operator cancel request condition.

The innermost level called read IN run IN DoATest IN Run IN Active IN Top is illustrated in FIG. 27. The diagram of FIG. 27 illustrates command signal monitoring for the acquisition and qualification of data from the analysis unit 302. Upon receiving a timer tick, a read signal condition is posted by the monitor. If the monitored signal is "ready" a post signal is generated, if not, a test failure signal may be posted otherwise the monitoring continues.

It will be appreciated by those of ordinary skill in the art that the software state diagrams of FIGS. 22–27 represent but a single preferred embodiment of an operating system and application software which may be employed by the instrument 10. It will be appreciated by those of ordinary skill in the art that the instrument 10 may use a different operating system, as well as different application specific software, if desired. Thus, the diagrams of FIGS. 22–27 are meant only as an illustration of a single preferred method of implementing the operating system software and application specific software of a preferred embodiment of the instrument 10. Because the software employed in the instrument 10 is a highly capable, standards-based platform, it is relatively easy to develop software upgrades and/or extensions that enable new or specialized applications and to download such newly developed software, upgrades and extensions into the instrument in the field utilizing the RS 232 input port 28 or the Ethernet port 29.

Basic Software Functions

The instrument 10 continually maintains calendar date and time with one second resolution, as long as minimum battery power is maintained. When the instrument 10 is in use, the current date and time are continually displayed on the LCD display 20. When a power failure has been detected, such as during battery replacement, the software does not restart until the operator has entered and confirmed the correct date and time. The records of all diagnostic tests perform by the instrument 10 contain the date and time at which the test was initiated. In addition, test protocols control timing with one millisecond resolution.

The software uses a numeric code for primary identification of test subjects. In the presently preferred embodiment, the nine digit social security number of the test subject is used because a nine digit number can be easily entered by an operator utilizing the alphanumeric keys 18 on the front panel 17 of the instrument 10. However, the software also has the capability of storing up to fifty characters of additional information for each test subject. Such additional information may include the person's name, zip code, telephone number, etc. Subject identifying information can also be entered into the instrument 10 utilizing the barcode scanner 32. If the barcode scanner 32 is used the software recognizes the identification information which is then displayed on the LCD display 20 for confirmation by the operator. The test subject may also be identified by recalling a previous test performed of the same subject which has previously been stored in the memory of the instrument 10. In any event, the identity of the test subject must be present and displayed on the LCD display screen 20 immediately before a test is performed.

The software also stores a ten digit numeric code which uniquely identifies the operator of the instrument as part of each test record. Again, the operator code can be entered by the operator using the alphanumeric keys 18 or the barcode scanner 32.

As stated above, each test cell 300 includes a barcode label 101 which includes a barcoded character string, which encodes the particular type of test for the test cell 300, an expiration date for the test cell, a test cell serial number, which may include a lot number, as A well as other information pertaining to the particular test cell 300. Taken together, the information presented in the barcoded character string uniquely identifies each test cell, as well as the particular test which may be performed utilizing the particular test cell. The test cell information may be entered into the instrument using the scanner 32 just prior to the test cell 300 being inserted into the slot 34 on the instrument 100. The information read from the test cell barcode 101 is also recorded as part of the test result. Upon receiving the test cell information, the software immediately compares the information received from the test cell barcode 101 to all stored test records and rejects the test cell 300 if that test cell has been read before. The software also uses the information read from the test cell barcode 101 to identify the particular test to be performed and to select the appropriate test protocol including test parameters, incubation times, calibration times, voltage limits, etc. for the particular test to be performed. Information in the form of test control tables, is stored in the memory 502 for each diagnostic test, which could potentially be performed utilizing the instrument 10.

In the performance of a diagnostic test, the operator enters the test subject identification information or selects information from a stored list, such that the identification information is displayed on the LCD display 20. The identification information is displayed on the display 20 and must be confirmed by the operator before the test can proceed. The operator then fills the test cell 300 with a sample of the test subject's blood or other bodily fluid and then scans the test cell barcode 101 using the barcode scanner 32. the software checks the scanned test cell barcode 101 to confirm that the test cell 300 has not been used before. When the speaker 510 of the barcode scanner 32 provides an audible beep, indicating a good scan and a good test cell 300, the operator immediately inserts the test cell 300 into the slot 34 with the proper orientation as described above. If the test cell 300 is properly inserted, the instrument 10 emits an audible beep and the test cell identification information read from the test cell barcode 101, as well as the test start date and time are displayed on the LCD display 20 and are added to the test result data.

The software permits only a predetermined elapsed time between the scanning of the test cell barcode 101 and the proper inserting of the test cell 300 into the slot 34 of the instrument 10. The elapsed time is adjustable, but is kept short enough to make it inconvenient for the operator to put the test cell 300 down between scanning and inserting as a way of making sure that the test cell 300 which is scanned is, in fact, the test cell 300 which is actually inserted into the instrument 10. If the operator takes too long to insert the test cell 300 into the slot 34, the instrument 10 emits a different audible beep meaning that the test cell 300 must be scanned again to restart the test and an appropriate message is displayed on the LCD display 20. If the operator fails to rescan and insert the test cell 300 within a reasonable time interval thereafter, the test is recorded as having failed, which automatically invalidates any further use of the particular test cell 300. Preferably, operators of the instrument 10 understand that the scanning of the test cell barcode 101 and the insertion of the test cell 300 into the slot 34 is accomplished in a single, continuous operation to be completed as quickly as possible in order to minimize a potential for erroneous test results.

As previously mentioned, once the test cell 300 has been inserted into the instrument 10, the software checks the test cell 300 and the quality of the electrical contact by monitoring electrical signals from the test cell 300. If either of these checks fail the diagnostic test is aborted. The coded resistor 335 of the test cell 300 is also read to confirm that the resistance is appropriate for test cell 300 having the scanned barcode 101 since the resistor 335 in each test cell 300 is of a value specific for the particular test.

Assuming that the test cell 300 has been properly inserted, has not been used before and that all of the relevant test subject and other identification information has been properly entered and verified by the operator, the software then proceeds with the performance of the diagnostic test in the manner which has been described above. The test involves two particular stages, namely a calibration stage and an actual test reading stage. Each of the stages of the test may take several minutes or may be accomplished in less than one minute depending upon the particular test being performed and other factors. Both the calibration stage and the actual testing stage are accomplished by taking a series of voltage readings across the electrodes 330A, 330B within the electrode chambers 324A, 324B of the test cell 300 as previously described. Voltage readings are continuously obtained and are continuously compared to previous voltage readings during both the calibration stage and the actual test stage until the software determines that the voltage readings have stabilized for at least a predetermined time period. The stabilized voltage readings then become the actual analog test data. The analog test data is then provided to the A/D convertor 506 and the data is reduced to calibrated standard digital values entered into the test record and stored as the test results. The test is aborted if voltage readings, which are outside of a prescribed range for the particular test are obtained or if the voltage readings are unstable for a longer period of time then expected for the particular test.

Once the test data has been obtained and entered into the stored test record a message on the LCD display 20 prompts the operator to remove and properly discard the used test cell 300. Upon removal of the test cell 300, the test results, including all of the above-described identification and timing information may be printed by the printer 514. A diagnostic test can be aborted by the software at any stage if a sensor or any other hardware failure is detected or if electrical contact with the test cell 300 is lost. The test can also be cancelled by the operator at any stage. Aborted tests are also recorded in the test result file to prevent reuse of a previously used test cell 300.

As previously mentioned, the parameters which are utilized to conduct each actual test are specified within a test control table stored in the memory and selected based upon the identification information obtained from the particular test cell 300 inserted into the instrument 10. The parameters from the test control table specified how each step of the test data acquisition and analysis is to be performed, including alternate software routines where necessary. In this manner, new or modified test parameters can be installed by downloading new test control tables and, if necessary, supporting software modules, without modification of the basic operating software or application software. Each test control table defines an explicit calibration function which relates the readings applied to the A-D convertor 506 to a standardized test result and includes the units in which the test results are to be reported, as well as an expected normal range for the test results.

As previously mentioned, the instrument 10 has the capability of performing three different categories of diagnostic tests, namely, potentiometric, amperometric and conductometric. The above-described diagnostic test, which utilize test cell 300 is of the potentiometric type. In the potentiometric type of test, the voltage measured across the electrodes of the test cell 300 varies as a logarithm of the ion concentration. The ion concentration is measured by the change in the voltage when a solution of known concentration (i.e., the calibration fluid) is replaced by the unknown (i.e., the blood or other bodily fluid to be tested).

In an amperometric test, a test cell (hereinafter described), having a different structure is employed. In the amperometric test, the current flowing through the electrodes is proportional to the rate of diffusion of an oxidizible or reducible reagent to the surface of an electrode which is held at a constant voltage potential. The membrane associated with the electrode either generates the reagent or selectively allows the reagent to pass therethrough. A wide variety of biochemical reaction rates can be measured by coupling them to production or consumption of one of the source reagents. Useable source reagents include, hydrogen peroxide, glucose oxides, NADH and molecule oxygen. The rate of reagent production or diffusion is usually proportional to the concentration of the source reagent in the test solution. In general, the rate of diffusion is established by the concentration of the analysand in a generally linear fashion. The electrode system is calibrated by measuring a known solution, i.e., the calibrating fluid.

The conductometric test uses yet another test cell, which will hereinafter be described. In the conductometric test, matched chambers, one with intact cells and the other with lysed cells are employed. The conductivity of each chamber is measured utilizing alternating current at a frequency high enough to make capacitive impedance of the electrode-to-solution junction small as compared to the resistive impedance of the solution itself. In effect, a balancing bridge circuit is established, such that the change in differential voltage across the bridge circuit is determined as a fraction of the excitation voltage for making the desired measurement.

Test results are stored in the flash ROM memory 502 in text form as displayed on the LCD display 20. Each test record includes all of the above-identified test information including the identification of the test subject, the particular test performed, the date and time of the test, operator ID and either a standardized test result or an identification of why the test failed or was aborted. In addition, unless disabled by the operator, each test record is preferably automatically printed by the printer 514 when the test is completed to provide a complete hard copy of the test record. All test results from either successfully completed or failed tests, are stored in the flash ROM memory 502. The operator can recall the test results from the flash ROM memory 502 and reprint the test results using the alphanumeric keys 18 on the front panel 17 of the instrument 10. Preferably, the flash ROM memory 502 is large enough to store a substantial number of test records, preferably corresponding to at least the number of tests which could be expected to be performed in a normal week of diagnostic testing. Preferably a minimum of 1000 records may be stored. The operator cannot delete stored records. However, if the memory 502 is completely filled, the unit automatically recycles or writes over the oldest test record with any new test records which are developed. Stored test records can be read or deleted via the RS 232 port 28 or the ethernet port 29. As previously mentioned, a recalled test record can provide the subject identification data for setting up a new test particularly when the same subjects are tested repeatedly. This feature adds to the efficiency of the instrument 10 by reducing the need for reentering subject identification information.

The operator interface is menu driven in which a series of items selected by single key strokes are displayed on the LCD display 20. In most cases, the operator is given a yes/no choice by the menu with a "yes" being indicated by depressing the enter key 16 and a "no" being indicated by depressing the cancel key 15. The result of an operator selecting an item is either the display of a new, lower level menu which requires a further selection or the initiation of a selected action. In the present embodiment, the first item selectable on each menu is a return to the previous menu with the exception of the first or top menu which permits selection of power down of the instrument 10. As the instrument 10 is performing a selected action, the menu from the selected action remains on the LCD display 20 with the selected item being indicated with highlighting, an arrow, or the like. A separate prompt line shows any required operator action, as well as the progress of any automatic actions being taken by the instrument 10. A selected action may proceed through a series of steps with each step being indicated by a new prompt to the operator. The operator can abort any action at any time by pressing a "CANCEL" key 15. The actuation of the CANCEL key 15 may also allow selection of alternate menus.

Preprinted barcode data scanned from a test cell barcode 101 are accepted as valid if the barcode scanner 32 detects no barcode error during the scanning process and the data format of the barcode is valid. All other data entered, recalled or scanned by the operator are first displayed on the prompt line of the LCD display 20. The operator must press the enter key 16 to confirm the correctness of data displayed on the prompt line before the data is entered or may press the CANCEL key 15 to reject data displayed on the prompt line.

Test information, whether prospective, in process or completed, is displayed on a separate portion of the LCD display 20 in a fixed, text format that includes the identifying information as described above. Elements of the test record which are not yet completed are either left blank or displayed as "unknown" until the test is completed.

Conservation of the battery power is an important concern which is addressed by the operating software at two levels. First, the current battery charge level as obtained from the battery monitor 530 is provided to the user on a periodic or continuous basis. The software also provides specific prompts to the operator to initiate a recharging of the battery pack 524 when the battery monitor 530 indicates that the battery charge level has fallen below a predetermined safe limit. Further, the software precludes the initiation of a new diagnostic test when the battery charge level in the battery pack 524 is to low for the safe completion of a diagnostic test without risking a malfunction of the analysis station 302, printer 514 or other software or hardware function associated with the diagnostic test.

The software also directly controls the power supplied to the various peripheral devices including the printer 514, the barcode scanner 32, the analysis station 32, the LCD display 20, particularly the screen backlight and the microprocessor 500 and selectively switches off the supply of power when the functions of the peripheral devices are not needed for current operation of the instrument 10. The software also places the entire instrument 10 into a "power down" state upon receiving an operator command or after a predetermined period of inactivity of the instrument 10. The power down state differs from the complete absence of power in that the date/time clock continues to run and the volatile DRAM memory 504 is maintained. However, when the power down occurs all software activity ceases and the LCD display 20 is blank. The operator may "power up" the unit by pressing a key on the front panel which results in the software restarting at the top menu. As previously mentioned, upon detection of the restoration of battery power after a total power loss, the software requires the operator to first enter the correct date and time before any other actions may be taken. Because the LCD display 20 constantly displays the current date and time whenever the instrument 10 is powered up, there is no need for a separate power indicator. In the present embodiment, the time period set for the instrument 10 to automatically power down based on a period of inactivity depends upon which menu is displayed. If the top menu, containing a power off item is displayed, the automatic power down time is short, in the present embodiment thirty seconds of inactivity. If any of the other menus or a test result is displayed, a longer period of time, in the present embodiment two minutes is required before the instrument 10 is powered down. The delay periods are adjustable using an options menu.

The LCD display 20 includes a backlight which is controlled semi-automatically according to an operator selected preference. Options include, always off, always on and automatic, which turns the backlight on at any key press and turns the backlight off again after an adjustable number of seconds have elapsed. When the system options menu is activated by holding a key down for three seconds, the LCD display backlight is always switched on.

The test cell 300 as shown in FIGS. 5–8 and as described in detail above is best suited for use in the performance of electrochemical diagnostic tests which are of the potentiometric type in which voltage measurements are concurrently taken with respect to a first fluid (the calibration fluid) in a first electrode chamber 324A and a fluid to be analyzed (i.e., blood or other fluid) in a second, separate electrode chamber 324B. However, when conducting an electrochemical diagnostic test of the amperometric type, a slightly different test cell (not shown) is employed. The employed amperometric test is structurally substantially the same as test cell 300 with one exception. In the amperometric test cell, only a single electrode chamber is provided with the two electrodes being positioned at spaced locations within the single electrode chamber. The fluid passageways for conducting the calibration fluid and for conducting the blood or other fluid to be analyzed both flow into the single electrode chamber. Likewise, overflow from the single electrode chamber flows through a single fluid passageway to the serpentine passageway 326. The remainder of the amperometric test cell is as described above in connection with test cell 300. The amperometric test cell is installed into the analysis station 302 in the same manner as described above and the flow of calibration fluid and blood or other fluid to be analyzed into and out of the single electrode chamber is achieved and controlled in the same manner as described above in connection with the first test cell 300. However, when performing a diagnostic test, amperometric measurements are taken with respect to current flowing between the two electrodes (i.e., through the fluid present in the electrode chamber) for performing the analysis. The measurement of the current flow through the calibration fluid may be taken before or after the measurement of current flow through the blood or other fluid. In some circumstances, it is not necessary to measure current flow though the calibration fluid so that only a single measurement of current flow through the blood or other fluid being analyzed is taken. It will be appreciated by those of ordinary skill in the art that a suitable amperometric test cell can be constructed by a slight modification to the test cell 300 by joining together the two electrode chambers 324A and 324B into a single electrode chamber. No other modifications are required.

The analysis station functions essentially the same as with the use of test cell 300. However, when an amperometric test cell is used, it may be desirable to draw the calibration fluid back into the calibration fluid capsule 314 by moving the first slide member 366 outwardly as shown in FIG. 17. The removal of the calibration fluid from the electrode chamber facilitates insertion of the blood or other fluid to be analyzed into the single electrode chamber in the manner as shown in FIG. 19.

Figure 29:
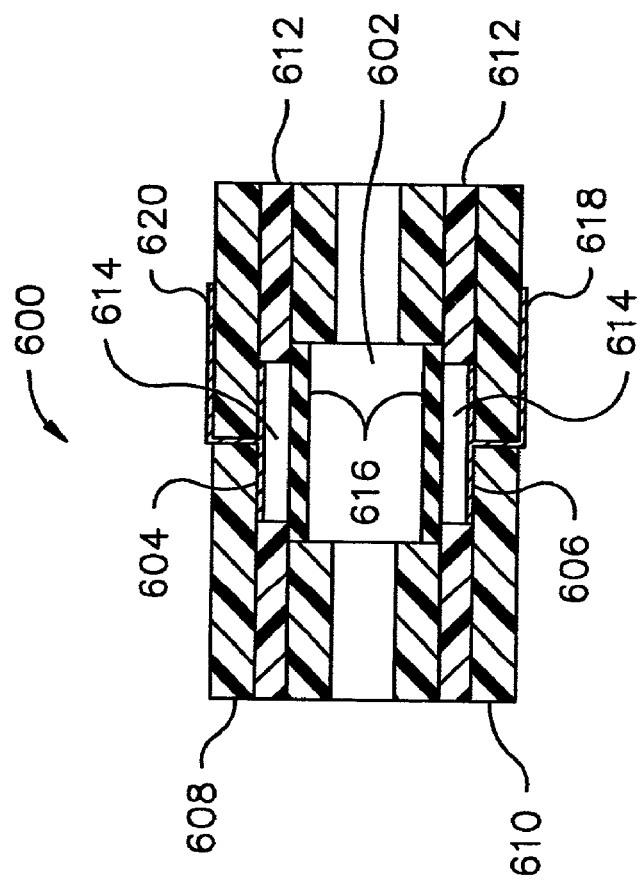
FIG. 29 is a cross-sectional view of an assembled version of the portion of the test cell shown in FIG. 28.
Figure 28:
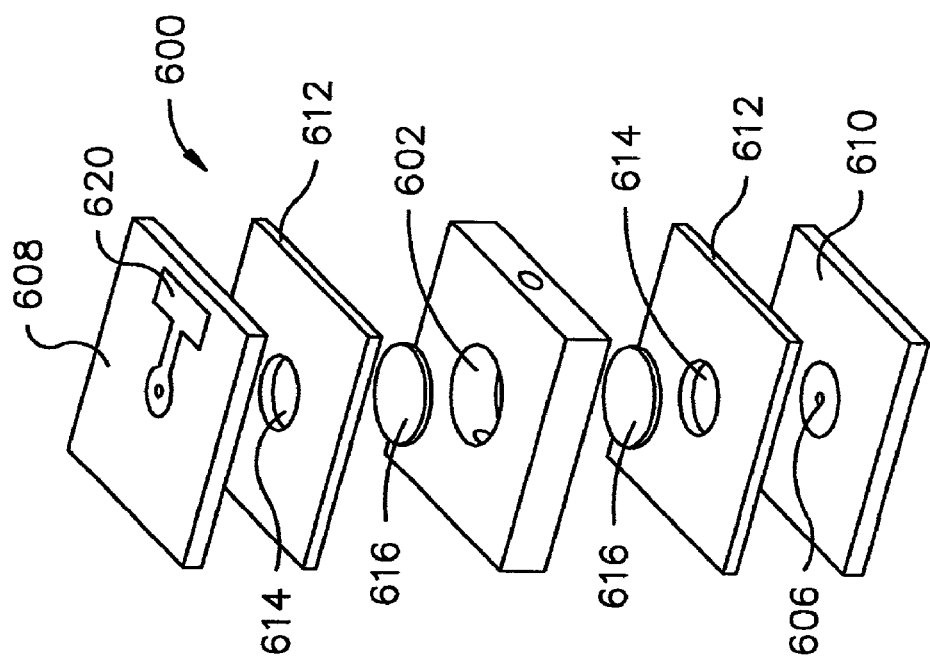
FIG. 28 is an exploded perspective view of a portion of an alternate embodiment of a test cell used to perform a diagnostic test.

FIGS. 28 and 29 illustrate a of test cell 600. Unlike the test cell 300 of FIGS. 5–8 which includes two electrode chambers, and the alternate, single electrode chamber test cell described above, the test cell 600 as shown in FIGS. 28 and 29 is axial in orientation rather than planar. That is, instead of the electrodes being side-by-side in generally the same plane in a single electrode chamber as in the above-described single electrode chamber test cell or in two separate electrode chambers 324A and 324B as in test cell 300, in test cell 600, a first electrode 604 is located above a single electrode chamber 602 and a second electrode 606 is located below the single electrode chamber 602. The first electrode 604 is mounted on a first printed circuit board or substrate 608 and the second electrode 606 is mounted on a second printed circuit board or substrate 610. The circuit boards or substrate 608 and 610 are preferably secured to the remainder of the test cell body 600 using two pieces of double sided tape 612 each having an appropriate opening 614 extending therethrough to create essentially the same "wells" as described above in connection with test cell 300. The portions of at least one of the openings 614 which face the electrode chamber 602 are covered by membranes 616. Similarly, electrode connections 618, 620 are provided on the opposite surfaces of the printed circuit boards 608, 610. A suitable electrolyte (not shown), which is preferably in the form of a gel, is initially positioned within each of the wells formed by the openings 614 in the double-sided tape 612. The remainder of the test cell 600 is as described above in connection with the test cell 300 and a diagnostic test is performed in the same manner as described above.

Figure 8:
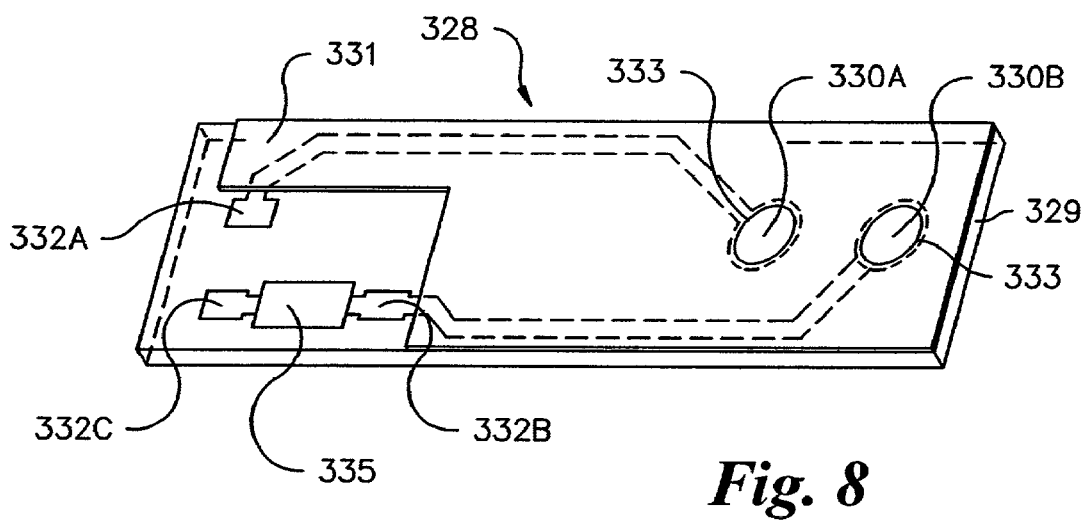
FIG. 8 is an enlarged perspective view of an electrode/contact pad assembly used in the test cell shown in FIG. 5.
Figure 30:
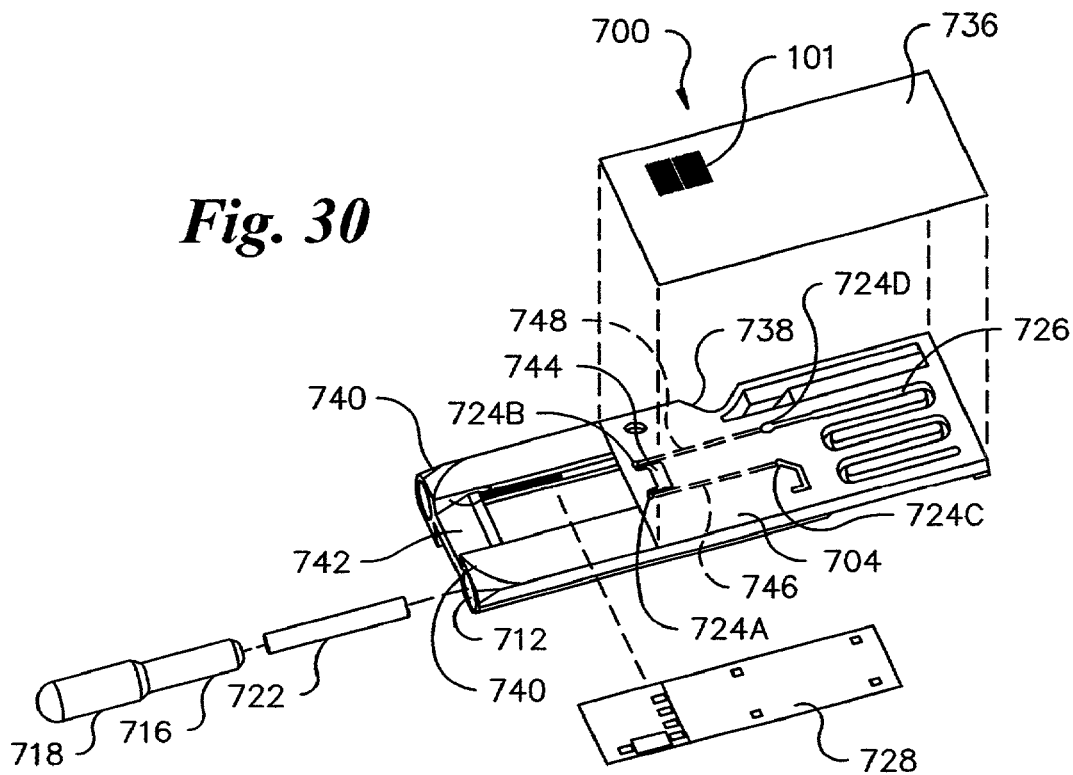
FIG. 30 is an exploded perspective view of another alternate embodiment of a test cell used to perform a diagnostic test.
Figure 31:
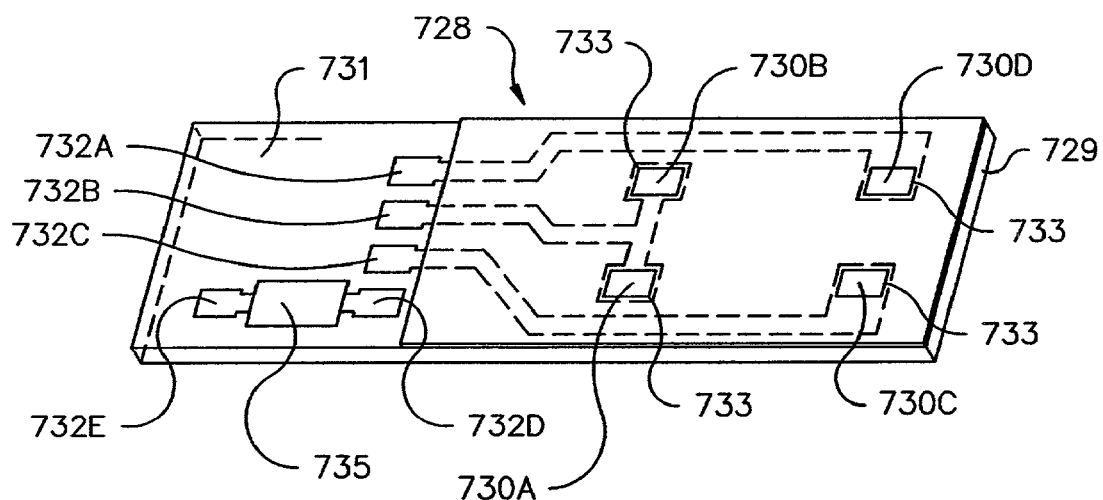
FIG. 31 is an enlarged perspective view of an electrode/contact pad assembly used in the test cell of FIG. 30.

Referring to FIGS. 30 and 31 there is shown another alternate embodiment of a disposable, single use test cell 700 for use within the above-described instrument 10 in accordance with the present invention. The test cell 700 is of a type well suited for use in connection with the conducting of a conductometeric diagnostic test. In particular, the test cell 700 is employed for a performance of a hematocrit diagnostic test upon the blood of a patient or other test subject. The test cell 700 as shown in FIGS. 30 and 31 is substantially structurally the same as the test cell 300 as shown in FIGS. 7 and 8 and as described in detail above. In particular, the test cell 700 includes a housing 704 which, with the exception of certain minor changes as hereinafter described, is structured the same as the housing 304 of test cell 300. Test cell 700 also includes an electrode/contact pad assembly 728, a specimen capsule 716 having a squeezable portion 718 and a cover member 736 substantially the same as described above in connection with test cell 300. However, unlike the above-described test cell 300, test cell 700 in accordance with the present embodiment does not include a calibration capsule for reason which will hereinafter become apparent.

As shown in FIG. 30, the test cell 700 includes a generally crescent shaped chamber 744, which initially contains a lysing agent, such as saphonin. The crescent shaped chamber 744, in turn, is connected on both ends to a pair of elongated capillary tubes or chambers 746 and 748. Each of the capillary chambers 746, 748 is generally rectangular or cylindrical and is of the exact same length and cross sectional area. Each of the ends of the crescent shaped chamber 744 includes a small electrode chamber 724A and 724B. The distal end of each of the capillary chambers 746 and 748 also includes a small electrode chamber 724C and 724D. The distal end of capillary chamber 746 is also fluidly connected through a suitable fluid passageway to the bore 712 of the test cell housing 704, which receives the specimen capsule 716. The distal end of capillary chamber 748 is also connected through a fluid passageway to the serpentine passageway 726 employed for receiving overflow or excess blood or other bodily fluid in a manner as described above. The physical structure of the test cell 700, including the beveled portions 740, 742, cutout portion 738 and the like is the same as described above in connection with the test cell 300 so that test cell 700 may be received within the analysis station 302 in the manner as described above.

FIG. 31 shows the electrode/contact pad assembly 728 of the test cell 700. The electrode/contact pad assembly 728 includes a substrate 729 and a dielectric layer 731 which covers a substantial portion of the substrate. Four electrodes 730A, 730B, 730C and 730D are located on the substrate 729, so as to be aligned with the respective electrode chambers 724A, 724B, 724C and 724D within the test cell housing 704 when the electrode/contact pad assembly 728 is secured to the test cell housing 704. As with test cell 300, suitable openings 733 extend through the dielectric layer 731 around the electrodes 730A, 730B, 730C and 730D to establish small "wells" for receiving fluid therein and to facilitate electrical contact between the electrodes 730A, 730B, 730C and 730D and fluid within the capillary chambers 746, 748 and electrode chambers 724A, 724B, 724C and 724D. Unlike test cell 300, the electrode/contact pad assembly 728 includes five electrical contact 732A, 732B, 732C, 732D and 732E. Contacts 732D and 732E are electrically connected to either end of a resistor 735, which functions as described above to verify the type of test cell which is inserted into the instrument 10. Contact 732A is connected to electrode 730D, contact 732B is connected to electrodes 730A and 730B and contact 732C is connected to electrode 730C.

To use the test cell 700, a sample of blood is collected within the specimen capsule 716 as described above and the specimen capsule 716 is installed within the bore 712. Thereafter, the test cell 700 is inserted within the analysis station 302 in the manner described above in connection with test cell 300. Once the test cell 700 is appropriately installed within the analysis station 302 and all of the appropriate checks have been performed, the diagnostic test begins by the analysis station 302 causing blood from the specimen capsule 716 to flow through the tube 722 through the passageway, through capillary chamber 746 and into the crescent shaped chamber 744. When the blood enters the crescent shaped chamber 744, the blood is lysed by the lysing agent. As blood continues to flow into the capillary chamber 746, lysed blood from the crescent shaped chamber 744 is forced into the second capillary chamber 748 and, if necessary, into the serpentine passageway 726. Once the capillary chamber 748 is filled with lysed blood and the other capillary chamber 746 is filled with whole blood, the diagnostic test is performed by measuring differences in conductivity between the whole blood and the lysed blood. The conductivity readings are obtained from the electrodes 730A, 730B, 730C and 730D which are located on both ends of the capillary chambers 746, 748. The conductivity readings are obtained from the test cell 700 through the electrical contacts 732A, 732B and 732C through suitable signal conditioning circuitry, A/D convertor, etc. in the same manner as described above in connection with test cell 300. Of course, in the performance of a diagnostic test utilizing test cell 700, a suitable test protocol must be used. The test protocol, which is normally stored in the memory of the instrument 10 is recalled based upon the information scanned from the barcode 101 on the cover 736 of test cell 700. The diagnostic test is otherwise conducted in substantially the same manner as described above in connection with test cell 300. If desired, the electrode locations and capillary chamber dimensions could be modified to accept small quantities of blood from a finger stick or other limited source.

From the foregoing description, it can be seen that the present invention comprises a novel medical diagnostic system comprising a self-contained, hand-held portable instrument and an associated disposable test cells. The present invention is capable of providing a variety of real time, medical diagnostic tests with respect to blood or other fluid from humans or animals. It will be appreciated by those of ordinary skill in the art that changes and modifications may be made to the embodiments described above without departing from the spirit and scope of the invention. Therefore, the present invention is not limited to the embodiments described above but is intended to cover all such modifications within the scope and spirit of the appended claims.

We claim:

1. A system for conducting a plurality of different medical diagnostic tests, the system comprising:

a hand held portable, self contained electronic instrument for engaging any one of a plurality of disposable test cells, each test cell containing a fluid to be tested, the instrument for performing a diagnostic test selected from said plurality of tests upon the fluid within a selected test cell, the instrument including a reader which reads indicia on the selected test cell prior to engagement of the test cell, the diagnostic test to be performed being selected by the instrument based upon identification information obtained from the indicia on the selected test cell, the instrument further including a unique identification code that provides positive identification of each test result provided by the instrument and the instrument being configured to output data of each test result combined with the unique identification code; and a plurality of disposable, single use test cells each test cell for receiving fluid to be diagnostically tested, each test cell including identification information including indicia indicative of a particular diagnostic test to be performed upon the fluid contained therein, the indicia on each test cell being unique to each medical diagnostic test which may be performed and unique with respect to each test cell which may be used to perform the same medical diagnostic test so that no two test cells contain the same indicia, each test cell being sized and shaped for engagement by the instrument, the instrument, upon reading the unique indicia of a selected test cell comparing the identification information from the read indicia to identification information from indicia read from all previously selected test cells and proceeding with the selected diagnostic test only if the selected test cell has not been previously used.

2. The system as recited in claim 1 wherein the instrument comprises a housing including an opening for receiving and engaging at least a portion of the test cell (the instrument further including a unique identification code to provide positive identification of all test results obtained using the instrument) therein.

3. The system as recited in claim 2 wherein the opening in the instrument housing is sized and shaped for receiving the portion of the test cell with a predetermined orientation which precludes insertion of the test cell therein with any other orientation.

4. The system as recited in claim 2 wherein the housing includes electrical contacts for engaging corresponding electrical contacts on the test cell when the test cell is inserted within the opening of the instrument.

5. The system as recited in claim 1 wherein the instrument includes a processor and a memory, the memory storing data and instructions for the performance of each of the plurality of different diagnostic tests, the processor accessing the memory to obtain data and instructions for the performance of the selected test based upon the information obtained from an engaged test cell.

6. The system as recited in claim 1 wherein each test cell includes at least one chamber for receiving fluid to be tested, the chamber containing at least two electrodes for the performance of ion selective analysis on the fluid within the test cell chamber.

7. The system as recited in claim 6 wherein each test cell further includes a source of calibration fluid for insertion into the chamber for calibration of the electrodes.

8. The system as recited in claim 7 wherein the calibration fluid is inserted into the test cell chamber for calibration of the electrodes after the fluid to be tested is received within the chamber.

9. The system as recited in claim 7 wherein the instrument controls the insertion of the calibration fluid into the test cell chamber.

10. The system as recited in claim 9 wherein the instrument includes an actuator which is connected to the test cell when the test cell is inserted into the instrument such that the actuator causes fluid to flow into the test cell chamber.

11. The system as recited in claim 7 wherein the instrument controls the length of time that the calibration fluid remains within the test cell chamber for calibration of the electrodes.

12. The system as recited in claim 7 wherein the type of calibration fluid contained within the test cell is determined by the particular test to be performed using the test cell.

13. The system as recited in claim 7 wherein the calibration fluid is inserted into the test cell chamber for calibrating the electrodes before the fluid to be tested is received within the chamber.

14. The system as recited in claim 6 wherein at least one of the electrodes is covered by an electrolyte, the composition of which is determined by the particular test to be performed utilizing the test cell.

15. The system as recited in claim 14 wherein the electrolyte is in the form of a gel impregnated with a selected ionic material.

16. The system as recited in claim 14 wherein the electrolyte is covered by a ion selective membrane so that the fluid within the chamber to be tested contacts the ion selective membrane.

17. The system as recited in claim 16 wherein the ion selective membrane is comprised of a polymeric material impregnated with chemical species determined by the particular test to be performed utilizing the test cell.

18. The system as recited in claim 6 wherein the electrodes are in electrical contact with the instrument when the test cell is engaged by the instrument.

19. The system as recited in claim 18 wherein the instrument includes electrical circuitry for receiving one of voltage, current and conductivity measurements from the electrodes within the test cell.

20. The system as recited in claim 6 wherein the instrument compares the conductivity between one pair of electrodes and another reference pair of electrodes.

21. The system as recited in claim 6 wherein the instrument measures current flowing between two electrodes maintained at a controlled voltage potential.

22. The system as recited in claim 1 wherein the indicia is a barcode on each test cell and wherein the instrument includes a barcode scanner for reading the barcode on the test cell.

23. The system as recited in claim 1 wherein the instrument includes a display for displaying the results of diagnostic tests performed by the instrument.

24. The system as recited in claim 23 wherein the display is comprised of a liquid crystal display.

25. The system as recited in claim 1 wherein the instrument includes an input device to facilitate inputting of information into the instrument.

26. The system as recited in claim 25 wherein the input device is an alphanumeric keyboard.

27. The system as recited in claim 1 wherein the instrument includes a printer for printing the results of diagnostic tests performed by the instrument.

28. The system as recited in claim 27 wherein the printer comprises a thermal printer.

29. The system as recited in claim 1 wherein the instrument includes an input/output port for communicating with other devices.

30. The system as recited in claim 29 wherein the input/output port comprises at least one of an RS 232 interface and an Ethernet interface.

31. The system as recited in claim 1 wherein the instrument includes an internal power source.

32. The system as recited in claim 31 wherein the power source comprises at least one rechargeable battery.

33. The system as recited in claim 32 wherein the instrument further includes a recharger for recharging the at least one rechargeable battery.

* * * * *